US008084470B2

(12) United States Patent
Merla et al.

(10) Patent No.: US 8,084,470 B2
(45) Date of Patent: Dec. 27, 2011

(54) SUBSTITUTED NICOTINAMIDE COMPOUNDS AND USES THEREOF

(75) Inventors: Beatrix Merla, Aachen (DE); Sven Kuehnert, Dueren (DE); Robert Frank, Aachen (DE); Dagmar Kaulartz, Stolberg (DE); Wolfgang Schroeder, Aachen (DE); Gregor Bahrenberg, Monschau-Konzen (DE); Klaus Schiene, Juechen (DE)

(73) Assignee: Gruenenthal GmbH, Aachen (DE)

( * ) Notice: Subject to any disclaimer, the term of this patent is extended or adjusted under 35 U.S.C. 154(b) by 460 days.

(21) Appl. No.: 12/212,369

(22) Filed: Sep. 17, 2008

(65) Prior Publication Data

US 2009/0076086 A1 Mar. 19, 2009

Related U.S. Application Data

(60) Provisional application No. 60/972,989, filed on Sep. 17, 2007.

(30) Foreign Application Priority Data

Sep. 17, 2007 (DE) .......................... 10 2007 044 277

(51) Int. Cl.
*C07D 409/14* (2006.01)
*A61K 31/444* (2006.01)
(52) U.S. Cl. ..................... 514/332; 546/255; 546/268.1; 546/275.4; 546/280.4; 514/336; 514/341; 514/342
(58) Field of Classification Search .................. None
See application file for complete search history.

(56) References Cited

U.S. PATENT DOCUMENTS 6,630,495 B1 * 10/2003 Cooke et al. .................. 514/357
2002/0128277 A1 9/2002 Dworetzky et al.

FOREIGN PATENT DOCUMENTS

WO WO 99/24404 5/1999
WO WO 2005/023802 A1 3/2005

OTHER PUBLICATIONS

G. Blackburn-Munro et al., "The anticonvulsant retigabine attenuates nociceptive behaviours in rat models of persistent and neuropathic pain", European Journal of Pharmacology, 460 (2003) 109-116.
T. Coderre et al., "Contribution of central neuroplasticity to pathological pain: review of clinical and experimental evidence", Pain, 52 (1993) 259-285.

R. Dost et al., "The anti-hyperalgesic activity of retigabine is mediated by KCNQ potassium channel activation", Naunyn-Schmiedeberg's Arch Pharmacol, (2004) 369: 382-390.
D. Dubuisson et al., "The Formalin Test: A Quantitative Study of the Analgesic Effects of Morphine, Meperidine, and Brain Stem Stimulation in Rats and Cats." Pain, 4 (1977) 161-174.
V. Gribkoff, "The therapeutic potential of neuronal KCNQ channel modulators", Expert Opinion Ther. Targets, (2003) 7(6): 737-748.
M.P.G. Korsgaard et al., "Anxiolytic Effects of Maxipost (BMS-204352) and Retigabine via Activation of Neuronal Kv7 Channels", The Journal of Pharmacology and Experimental Therapeutics, vol. 314, No. 1, 2005, 282-292.
A. Nielsen et al., "Pharmacological characterisation of acid-induced muscle allodynia in rats", European Journal of Pharmacology, 487 (2004) 93-103.
G. Passmore et al., "KCNQ/M Currents in Sensory Neurons: Significance for Pain Therapy", The Journal of Neuroscience, Aug. 6, 2003, 23 (18): 7227-7236.
O.P. Hamill et al., "Improved Patch-Clamp Technologies for High-Resolution Current Recording from Cells and Cell-Free Membrane Patches", European Journal of Physiology (1981) 391: 85-100.
T. Streng et al., "Urodynamic Effects of the K+ Channel (KCNQ) Opener Retigabine in Freely Moving, Conscious Rats", The Journal of Urology, (2004) vol. 172, 2054-2058.
A. Wickenden et al., "KCNQ potassium channels: drug targets for the treatment of epilepsy and pain", Expert Opinion Ther. Patents (2004) 14(4): 457-469.

* cited by examiner

*Primary Examiner* — Zinna Northington Davis
(74) *Attorney, Agent, or Firm* — Crowell & Moring LLP

(57) ABSTRACT

Substituted nicotinamide compounds corresponding to formula I

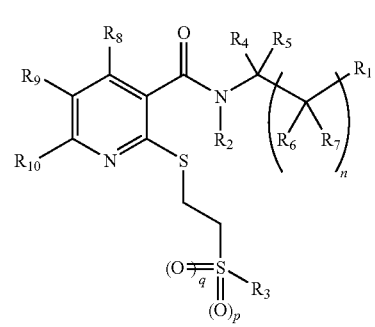

a process for their preparation, pharmaceutical compositions containing these compounds, and the use thereof for the treatment or inhibition conditions such as pain, epilepsy, migraine, anxiety states, or urinary incontinence.

18 Claims, No Drawings

SUBSTITUTED NICOTINAMIDE COMPOUNDS AND USES THEREOF

CROSS REFERENCE TO RELATED APPLICATIONS

This application claims priority based on U.S. provisional patent application No. 60/972,989, filed Sep. 17, 2007. Priority is also claimed based on Federal Republic of Germany patent application no. DE 10 2007 044 277.9, likewise filed Sep. 17, 2007.

BACKGROUND OF THE INVENTION

The present invention relates to substituted nicotinamide compounds, to a process for their preparation, to medicaments comprising these compounds and to the use of these compounds in the preparation of medicaments.

The treatment of pain, in particular of neuropathic pain, is of great importance in medicine. There is a worldwide need for effective pain therapies. The urgent need for action for a target-orientated treatment of chronic and non-chronic states of pain appropriate for the patient, by which is to be understood successful and satisfactory pain treatment for the patient, is also documented in the large number of scientific works which have recently been published in the field of applied analgesics and of fundamental research into nociception.

A pathophysiological feature of chronic pain is the over-excitability of neurons. Neuronal excitability is influenced decisively by the activity of K$^+$ channels, since these determine decisively the resting membrane potential of the cell and therefore the excitability threshold. Heteromeric K$^+$ channels of the molecular subtype KCNQ2/3 (Kv7.2/7.3) are expressed in neurons of various regions of the central (hippocampus, amygdala) and peripheral (dorsal root ganglia) nervous system and regulate the excitability thereof. Activation of KCNQ2/3 K$^+$ channels leads to a hyperpolarization of the cell membrane and, accompanying this, to a decrease in the electrical excitability of these neurons. KCNQ2/3-expressing neurons of the dorsal root ganglia are involved in the transmission of nociceptive stimuli from the periphery into the spinal marrow (Passmore et al., J. Neurosci. 2003; 23(18): 7227-36). It has accordingly been possible to detect an analgesic activity in preclinical neuropathy and inflammatory pain models for the KCNQ2/3 agonist retigabine (Blackburn-Munro and Jensen, Eur J Pharmacol. 2003; 460(2-3); 109-16; post et al., Naunyn Schmiedebergs Arch Pharmacol 2004; 369(4): 382-390). The KCNQ2/3 K$^+$ channel thus represents a suitable starting point for the treatment of pain; in particular of pain selected from the group consisting of chronic pain, neuropathic pain, inflammatory pain and muscular pain (Nielsen et al., Eur J Pharmacol. 2004; 487(1-3): 93-103), in particular of neuropathic and inflammatory pain.

Moreover, the KCNQ2/3 K$^+$ channel is a suitable target for therapy of a large number of further diseases, such as, for example, migraine (US2002/0128277), cognitive diseases (Gribkoff, Expert Opin Ther Targets 2003; 7(6): 737-748), anxiety states (Korsgaard et al., J Pharmacol Exp Ther. 2005, 14(1): 282-92), epilepsy (Wickenden et al., Expert Opin Ther Pat 2004; 14(4): 457-469) and urinary incontinence (Streng et al., J Urol 2004; 172: 2054-2058).

SUMMARY OF THE INVENTION

It was an object of the present invention, therefore, to provide novel compounds which are suitable in particular as pharmacological active ingredients in medicaments, preferably in medicaments for the treatment of disorders or diseases which are at least partly mediated by KCNQ2/3 K$^+$ channels.

It has now been found, surprisingly, that substituted nicotinamide compounds of the general formula I given below are suitable for the treatment of pain and also have an excellent affinity for the KCNQ2/3 K$^+$ channel and are therefore suitable for the treatment of disorders or diseases which are at least partly mediated by KCNQ2/3 K$^+$ channels.

The present invention accordingly provides substituted nicotinamide compounds corresponding to formula I

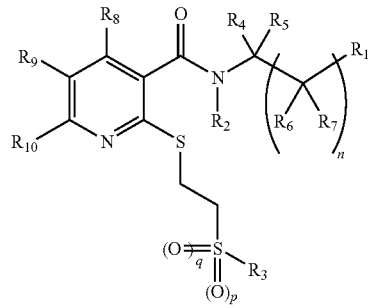

wherein
n=0, 1 or 2;
p=0 or 1
q=0 or 1,
R$^1$ denotes aryl or heteroaryl, unsubstituted or mono- or poly-substituted; C$_{1-6}$-alkyl, C$_{3-10}$-cycloalkyl or heterocyclyl, unsubstituted or mono- or poly-substituted;
R$^2$ denotes H; C$_{1-6}$-alkyl, unsubstituted or mono- or poly-substituted;
R$^3$ denotes aryl or heteroaryl, unsubstituted or mono- or poly-substituted; C$_{1-6}$-alkyl or C$_{3-10}$-cycloalkyl, in each case unsubstituted or mono- or poly-substituted;
R$^4$, R$^5$, R$^6$ and R$^7$ each independently denote H or C$_{1-6}$-alkyl which may be unsubstituted or mono- or poly-substituted;
R$^8$, R$^9$ and R$^{10}$ each independently denote H, F, Cl, Br, O—C$_{1-6}$-alkyl, CF$_3$, OCF$_3$, SCF$_3$, or C$_{1-6}$-alkyl;
with the proviso that
if R$^3$ is 3-trifluoromethylphenyl or 4-trifluoromethyl-2-pyridyl, R$^2$, R$^4$ and R$^5$ denote H and n denotes 0, then R$^1$ is not 2-pyridyl or 2-thienyl; and
if R$^3$ is phenyl or methyl, R$^2$, R$^4$ and R$^5$ are each H, and n denotes 0, then R$^1$ is not 2-thienyl;
in the form of the racemate; of the enantiomers, diastereoisomers, mixtures of the enantiomers or diastereoisomers or of an individual enantiomer or diastereoisomer; of the bases and/or salts of physiologically acceptable acids.

In connection with "phenyl", "phenyloxy", "benzyl", "benzyloxy", "alkylaryl", the term in each case includes the unsubstituted structure as well as the structure substituted by F, Cl, OCH$_3$, CF$_3$, OCF$_3$, SCF$_3$ and CH$_3$.

Within the scope of this invention, the expression "C$_{1-6}$-alkyl" includes acyclic saturated or unsaturated hydrocarbon radicals, which can be branched- or straight-chained and unsubstituted or mono- or poly-substituted, having from 1 to 6 carbon atoms, i.e. C$_{1-6}$-alkanyls, C$_{2-6}$-alkenyls and C$_{2-6}$-alkynyls. In this context, alkenyls contain at least one C—C double bond and alkynyls contain at least one C—C triple bond. Alkyl is advantageously selected from the group comprising methyl, ethyl, n-propyl, 2-propyl, n-butyl, isobutyl, sec-butyl, tert-butyl, n-pentyl, isopentyl, neopentyl, hexyl, ethylenyl (vinyl), ethynyl, propenyl (—CH$_2$CH═CH$_2$, —CH=CH—CH$_3$, —C(=CH$_2$)—CH$_3$), propynyl (—CH—C≡CH, —C≡C—CH$_3$), butenyl, butynyl, pentenyl, pentynyl, hexenyl and hexynyl. Methyl, ethyl and tert-butyl are particularly advantageous.

For the purposes of this invention, the expression "cycloalkyl" or "C$_{3-10}$-cycloalkyl" denotes cyclic hydrocarbons having 3, 4, 5, 6, 7, 8, 9 or 10 carbon atoms, wherein the hydrocarbons can be saturated or unsaturated (but not aromatic), unsubstituted or mono- or poly-substituted, bridged or unbridged. C$_{3-8}$-Cycloalkyl is advantageously selected from the group containing cyclopropyl, cyclobutyl, cyclopentyl, cyclohexyl, cycloheptyl, cyclooctyl, cyclopentenyl, cyclohexenyl, cycloheptenyl, cyclooctenyl, bicyclo[3.3.1]heptanyl and adamantyl.

The term "heterocyclyl" includes saturated or unsaturated (but not aromatic) cycloalkyls having from three to eight ring members, in which one or two carbon atoms have been replaced by a hetero atom S, N or O. Heterocyclyl radicals from the group tetrahydropyranyl, dioxanyl, dioxolanyl, morpholinyl, piperidinyl, piperazinyl, pyrazolinonyl and pyrrolidinyl are advantageous.

Within the scope of this invention, the expression "aryl" denotes aromatic hydrocarbons having up to 14 ring members, inter alia phenyls and naphthyls. The aryl radicals can also be fused with further saturated, (partially) unsaturated or aromatic ring systems, which optionally contains one or two hetero atoms from the group O, N and S. Each aryl radical can be unsubstituted or mono- or poly-substituted, where the substituents on the aryl can be identical or different and can be in any desired and possible position of the aryl. Aryl is advantageously selected from the group containing phenyl, 1-naphthyl, 2-naphthyl, each of which can be unsubstituted or mono- or poly-substituted.

The expression "heteroaryl" represents a 5-, 6- or 7-membered cyclic aromatic radical which contains at least 1, optionally also 2, 3, 4 or 5 hetero atoms, where the hetero atoms are identical or different and the heterocyclic ring can be unsubstituted or mono- or poly-substituted; in the case of substitution on the heterocyclic ring, the substituents can be identical or different and can be in any desired and possible position of the heteroaryl. The heterocyclic ring can also be part of a bi- or poly-cyclic system having up to 14 ring members. Preferred hetero atoms are nitrogen, oxygen and sulfur. It is preferable for the heteroaryl radical to be selected from the group containing pyrrolyl, indolyl, furyl (furanyl), benzofuranyl, thienyl (thiophenyl), benzothienyl, benzothiadiazolyl, benzothiazolyl, benzotriazolyl, benzodioxolanyl, benzodioxanyl, phthalazinyl, pyrazolyl, imidazolyl, thiazolyl, oxadiazolyl, isoxazolyl, pyridyl, pyridazinyl, pyrimidinyl, pyrazinyl, indazolyl, purinyl, indolizinyl, quinolinyl, isoquinolinyl, quinazolinyl, carbazolyl, phenazinyl and oxadiazolyl, where the bonding to the compounds of the general structure I can be effected via any desired and possible ring member of the heteroaryl radical. Pyridyl, furyl and thienyl are particularly preferred.

In connection with "alkyl", "heterocyclyl" and "cycloalkyl", the term "substituted" is understood as meaning within the scope of this invention the replacement of a hydrogen radical by F, Cl, Br, I, —CN, NH$_2$, NH—C$_{1-6}$-alkyl, NH—C$_{1-6}$-alkyl-OH, C$_{1-6}$-alkyl, N(C$_{1-6}$-alkyl)$_2$, N(C$_{1-6}$-alkyl-OH)$_2$, NO$_2$, SH, S—C$_{1-6}$-alkyl, S-benzyl, O—C$_{1-6}$-alkyl, OH, O—C$_{1-6}$-alkyl-OH, =O, O-benzyl, C(=O)C$_{1-6}$-alkyl, CO$_2$H, CO$_2$—C$_{1-16}$-alkyl, phenyl, phenoxy, morpholinyl, piperidinyl, pyrrolidinyl or benzyl, where polysubstituted radicals are to be understood as meaning those radicals which are substituted several times, e.g. two or three times, either on different atoms or on the same atom, for example three times on the same carbon atom, as in the case of CF$_3$ or —CH$_2$CF$_3$, or at different places, as in the case of —CH(OH)—CH=CH—CHCl$_2$. Polysubstitution can be with the same or with different substituents.

In respect of "aryl" and "heteroaryl", "mono- or polysubstituted" is understood within the scope of this invention as meaning the replacement one or more times, e.g. two, three or four times, of one or more hydrogen atoms of the ring system by F, Cl, Br, I, CN, NH$_2$, NH—C$_{1-6}$-alkyl, NH—C$_{1-6}$-alkyl-OH, N(C$_{1-6}$-alkyl)$_2$, N(C$_{1-6}$-alkyl-OH)$_2$, NO$_2$, SH, S—C$_{1-6}$-alkyl, OH, O—C$_{1-6}$-alkyl, O—C$_{1-6}$alkyl-OH, C(=O)C$_{1-6}$-alkyl, C(=O)NHC$_{1-6}$-alkyl; o-pyridyl; C(=O)-aryl; C(=O)—N-morpholine; C(=O)-piperidine; (C=O)-pyrrolidine; (C=O)-piperazine; NHSO$_2$C$_{1-6}$-alkyl, NHCOC$_{1-6}$-alkyl, CO$_2$H, CH$_2$SO$_2$-phenyl, CO$_2$—C$_{1-6}$-alkyl, OCF$_3$, SCF$_3$, CF$_3$,

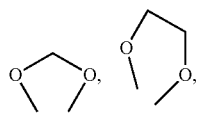

C$_{1-6}$-alkyl, pyrrolidinyl, piperidinyl, morpholinyl, benzyloxy, phenoxy, phenyl, pyridyl, alkylaryl, imidazolyl, pyrazolyl, thienyl or furyl; on one or optionally different atoms, where a substituent can itself optionally be substituted, but not with a further aryl or heteroaryl ring. Polysubstitution in this context is with the same or with different substituents. Preferred substituents for "aryl" or "heteroaryl" are F, Cl, Br, OCH$_3$, CF$_3$, OCF$_3$, SCF$_3$ and CH$_3$.

Within the scope of this invention, the term of salt formed with a physiologically acceptable acid is understood as meaning salts of the particular active ingredient with inorganic or organic acids which are physiologically acceptable—in particular when used in humans and/or mammals. The hydrochloride is particularly preferred. Examples of physiologically acceptable acids are: hydrochloric acid, hydrobromic acid, sulfuric acid, methanesulfonic acid, formic acid, acetic acid, oxalic acid, succinic acid, tartaric acid, mandelic acid, fumaric acid, maleic acid, lactic acid, citric acid, glutamic acid, 1,1-dioxo-1,2-dihydro1λ$^6$-benzo[d]isothiazol-3-one (saccharic acid), monomethylsebacic acid, 5-oxo-proline, hexane-1-sulfonic acid, nicotinic acid, 2-, 3- or 4-aminobenzoic acid, 2,4,6-trimethyl-benzoic acid, α-liponic acid, acetylglycine, hippuric acid, phosphoric acid and/or aspartic acid. Citric acid and hydrochloric acid are particularly preferred.

Preference is given within the scope of this invention to substituted nicotinamide compounds of the general formula I wherein n=0, 1 or 2;
p=0 or 1;
q=0 or 1;
R$^1$ denotes aryl or heteroaryl, unsubstituted or mono- or poly-substituted; C$_{1-6}$-alkyl, C$_{3-10}$-cycloalkyl or heterocyclyl, unsubstituted or mono- or poly-substituted;
R$^2$ denotes H; C$_{1-6}$-alkyl, unsubstituted or mono- or poly-substituted;
R$^3$ denotes aryl or heteroaryl, unsubstituted or mono- or poly-substituted; C$_{1-6}$-alkyl or C$_{3-10}$-cycloalkyl, in each case unsubstituted or mono- or poly-substituted;
R$^4$, R$^5$, R$^6$ and R$^7$ independently of one another denote H; C$_{1-6}$-alkyl, unsubstituted or mono- or poly-substituted;
R$^8$, R$^9$ and R$^{10}$ independently of one another denote H, F, Cl, Br, O—C$_{1-6}$-alkyl, CF$_3$, OCF$_3$, SCF$_3$, C$_{1-6}$-alkyl;

with the proviso that
if $R^3$ denotes 3-trifluoromethylphenyl or 4-trifluoromethyl-2-pyridyl, $R^2$, $R^4$ and $R^5$ each denote H, and n denotes 0, then $R^1$ is not 2-pyridyl or 2-thienyl; and
if $R^3$ denotes phenyl or methyl, $R^2$, $R^4$ and $R^5$ each denote H, and n denotes 0, then $R^1$ is not 2-thienyl;
wherein
"alkyl substituted", "heterocyclyl substituted" and "cycloalkyl substituted" denote the replacement of a hydrogen by F, Cl, Br, I, —CN, $NH_2$, NH—$C_{1-6}$-alkyl, NH—$C_{1-6}$-alkyl-OH, $C_{1-6}$-alkyl, $N(C_{1-6}$-alkyl$)_2$, $N(C_{1-6}$-alkyl-OH$)_2$, $NO_2$, SH, S—$C_{1-16}$-alkyl, S-benzyl, O—$C_{1-6}$-alkyl, OH, O—$C_{1-6}$-alkyl-OH, =O, O-benzyl, C(=O)$C_{1-6}$-alkyl, $CO_2H$, $CO_2$—$C_{1-6}$-alkyl, phenyl, phenoxy, morpholinyl, piperidinyl, pyrrolidinyl or benzyl; and
"aryl substituted" and "heteroaryl substituted" denote the replacement one or more times, e.g. two, three or four times, of one or more hydrogen atoms of the ring system by F, Cl, Br, I, CN, $NH_2$, NH—$C_{1-6}$-alkyl, NH—$C_{1-6}$-alkyl-OH, $N(C_{1-6}$-alkyl$)_2$, $N(C_{1-6}$-alkyl-OH$)_2$, $NO_2$, SH, S—$C_{1-6}$-alkyl, OH, O—$C_{1-6}$-alkyl, O—$C_{1-6}$alkyl-OH, C(=O)$C_{1-6}$-alkyl, C(=O)NH$C_{1-6}$-alkyl; o-pyridyl; C(=O)-aryl; C(=O)—N-morpholine; C(=O)-piperidine; (C=O)-pyrrolidine; (C=O)-piperazine; $NHSO_2C_{1-6}$-alkyl, $NHCOC_{1-6}$-alkyl, $CO_2H$, $CH_2SO_2$-phenyl, $CO_2$—$C_{1-6}$-alkyl, $OCF_3$, $SCF_3$, $CF_3$,

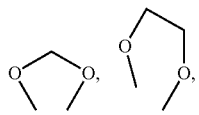

$C_{1-6}$-alkyl, pyrrolidinyl, piperidinyl, morpholinyl, benzyloxy, phenoxy, phenyl, pyridyl, alkylaryl, imidazolyl, pyrazolyl, thienyl or furyl.

Substituted nicotinamide derivatives of the general formula I are preferred in which p and q each denote 1 (sulfones).

Preference is also given to substituted nicotinamide derivatives of formula I in which p and q each denote 0 (thioethers).

Preference is further given to substituted nicotinamide compounds of formula I in which $R^8$, $R^9$ and $R^{10}$ each denote H.

Preference is given to substituted nicotinamide derivatives of formula I in which:
$R^1$ denotes pyrrolyl, furyl, thienyl, pyrazolyl, imidazolyl, thiazolyl, oxadiazolyl, isoxazolyl, pyridyl, pyrimidinyl, pyrazinyl, thiadiazolyl, oxazolyl, isothiazolyl, phenyl, naphthyl, cyclopropyl, cyclobutyl, cyclopentyl, cyclohexyl, cycloheptyl, tetrahydropyranyl, dioxanyl or $C_{1-6}$-alkyl, in each case unsubstituted or mono- or poly-substituted;
especially compounds in which:
$R^1$ denotes tert-butyl, phenyl, pyridyl, thienyl, furyl or cyclohexyl, unsubstituted or mono- or poly-substituted.

Particular preference is given to substituted nicotinamide derivatives of formula I in which:
$R^1$ denotes cyclohexyl; phenyl, unsubstituted or mono- or poly-substituted by F, $CH_3$, Cl, Br, $CF_3$, $OCH_3$, $SCF_3$ or $OCF_3$; pyridyl, thienyl or furyl, unsubstituted or mono- or poly-substituted by $CH_3$.

It is preferable for $R^2$ to represent $CH_3$ or H, in particular H.
It is further preferable for $R^4$, $R^5$, $R^6$ and $R^7$ independently of one another to represent H or $CH_3$, in particular H.
n preferably denotes 0 or 1, particularly preferably 0.

Preference is given also to substituted nicotinamide derivatives in which $R^3$ denotes aryl or heteroaryl, unsubstituted or mono- or poly-substituted, preferably
$R^3$ denotes phenyl or pyridyl, unsubstituted or mono- or poly-substituted, in particular phenyl mono- or poly-substituted by F, $CH_3$, $CF_3$, $OCF_3$, $OCH_3$, $SCF_3$ or Cl.

Particular preference is given to substituted nicotinamide derivatives in which $R^3$ denotes phenyl unsubstituted or substituted by $CF_3$ or $CH_3$.

Particular preference is given also to compounds in which the preferred definitions listed for the groups $R^1$ to $R^7$ are combined with one another.

Very particular preference is given to substituted nicotinamide compounds selected from the group consisting of:
1   2-(2-(phenylsulfonyl)ethylthio)-N-(pyridin-2-ylmethyl) nicotinamide
2   2-(2-(phenylsulfonyl)ethylthio)-N-(pyridin-4-ylmethyl) nicotinamide
3   N-(3-fluorophenethyl)-2-(2-(phenylsulfonyl)ethylthio) nicotinamide
4   N-methyl-N-(3-methylbenzyl)-2-(2-(phenylsulfonyl)ethylthio)nicotinamide
    N-(4-methylbenzyl)-2-(2-(phenylsulfonyl)ethylthio)nicotinamide
6   2-(2-(phenylsulfonyl)ethylthio)-N-(2-(trifluoromethyl) benzyl)nicotinamide
7   2-(2-(phenylsulfonyl)ethylthio)-N-(pyridin-3-ylmethyl) nicotinamide
8   N-(3,5-difluorobenzyl)-2-(2-(phenylsulfonyl)ethylthio) nicotinamide
9   N-methyl-N-phenethyl-2-(2-(phenylsulfonyl)ethylthio) nicotinamide
10  N-(3-methoxybenzyl)-N-methyl-2-(2-(phenylsulfonyl) ethylthio)nicotinamide
11  N-(2-fluorobenzyl)-2-(2-(phenylsulfonyl)ethylthio)nicotinamide
12  N-(3,4-difluorobenzyl)-2-(2-(phenylsulfonyl)ethylthio) nicotinamide
13  N-(3-bromobenzyl)-N-methyl-2-(2-(phenylsulfonyl)ethylthio)nicotinamide
14  N-(2-methoxybenzyl)-2-(2-(phenylsulfonyl)ethylthio) nicotinamide
15  N-(3-fluorobenzyl)-2-(2-(phenylsulfonyl)ethylthio)nicotinamide
16  N-(furan-2-ylmethyl)-N-methyl-2-(2-(phenylsulfonyl) ethylthio)nicotinamide
17  N-(4-methoxybenzyl)-2-(2-(phenylsulfonyl)ethylthio) nicotinamide
18  N-(2-chlorobenzyl)-2-(2-(phenylsulfonyl)ethylthio)nicotinamide
19  N-(3,4-dichlorobenzyl)-2-(2-(phenylsulfonyl)ethylthio) nicotinamide
20  N-(4-fluorobenzyl)-2-(2-(phenylsulfonyl)ethylthio)nicotinamide
21  N-(2-methoxyphenethyl)-2-(2-(phenylsulfonyl)ethylthio) nicotinamide
22  N-(2,6-difluorobenzyl)-2-(2-(phenylsulfonyl)ethylthio) nicotinamide
23  N-(2-methylbenzyl)-2-(2-(phenylsulfonyl)ethylthio) nicotinamide
24  N-(3,5-dimethoxybenzyl)-2-(2-(phenylsulfonyl)ethylthio)nicotinamide
25  N-(3-chlorobenzyl)-2-(2-(phenylsulfonyl)ethylthio)nicotinamide
26  N-(2,4-dichlorobenzyl)-2-(2-(phenylsulfonyl)ethylthio) nicotinamide 29 N-(4-chlorobenzyl)-2-(2-(phenylsulfonyl)ethylthio)nicotinamide
30 N-(2,3-dichlorobenzyl)-2-(2-(phenylsulfonyl)ethylthio)nicotinamide
31 N-(4-bromobenzyl)-N-methyl-2-(2-(phenylsulfonyl)ethylthio)nicotinamide
32 N-((1,3-dioxolan-2-yl)methyl)-N-methyl-2-(2-(phenylsulfonyl)ethylthio)-nicotinamide
33 N-benzyl-N-methyl-2-(2-tosylethylthio)nicotinamide
34 N-(pyridin-2-ylmethyl)-2-(2-tosylethylthio)nicotinamide
35 N-(pyridin-4-ylmethyl)-2-(2-tosylethylthio)nicotinamide
36 N-(thiophen-2-ylmethyl)-2-(2-tosylethylthio)nicotinamide
37 N-(3-fluorophenethyl)-2-(2-tosylethylthio)nicotinamide
38 N-methyl-N-(3-methylbenzyl)-2-(2-tosylethylthio)nicotinamide
39 N-(furan-2-ylmethyl)-2-(2-tosylethylthio)nicotinamide
40 N-(pyridin-3-ylmethyl)-2-(2-tosylethylthio)nicotinamide
41 N-(3,5-difluorobenzyl)-2-(2-tosylethylthio)nicotinamide
42 N-(3-methoxybenzyl)-N-methyl-2-(2-tosylethylthio)nicotinamide
43 N-(2-fluorobenzyl)-2-(2-tosylethylthio)nicotinamide
44 N-(3-methylbenzyl)-2-(2-tosylethylthio)nicotinamide
45 N-(3,4-difluorobenzyl)-2-(2-tosylethylthio)nicotinamide
46 N-(3-bromobenzyl)-N-methyl-2-(2-tosylethylthio)nicotinamide
47 N-(4-methoxybenzyl)-2-(2-tosylethylthio)nicotinamide
48 N-(2-chlorobenzyl)-2-(2-tosylethylthio)nicotinamide
49 N-(4-fluorobenzyl)-2-(2-tosylethylthio)nicotinamide
50 N-(3,5-dimethoxybenzyl)-2-(2-tosylethylthio)nicotinamide
51 N-(3-chlorobenzyl)-2-(2-tosylethylthio)nicotinamide
52 2-(2-tosylethylthio)-N-(3-(trifluoromethyl)benzyl)nicotinamide
54 N-benzyl-2-(2-(phenylsulfonyl)ethylthio)nicotinamide
55 N-benzyl-N-methyl-2-(2-(phenylsulfonyl)ethylthio)nicotinamide
56 N-(cyclohexylmethyl)-2-(2-(phenylsulfonyl)ethylthio)nicotinamide
57 2-(2-(phenylsulfonyl)ethylthio)-N-(1-(3-(trifluoromethyl)phenyl)ethyl)-nicotinamide
58 N-(2-cyclohexylethyl)-2-(2-(phenylsulfonyl)ethylthio)nicotinamide
59 2-(2-(cyclohexylthio)ethylthio)-N-(thiophen-2-ylmethyl)nicotinamide
60 N-(neopentyl)-2-(2-(phenylsulfonyl)ethylthio)nicotinamide
61 N-(5-methylfuran-2-ylmethyl)-2-(2-(phenylsulfonyl)ethylthio)nicotinamide
62 N-(furan-2-ylmethyl)-2-(2-(phenylsulfonyl)ethylthio)nicotinamide
63 2-(2-(phenylsulfonyl)ethylthio)-N-(tetrahydro-2H-pyran-4-ylmethyl)-nicotinamide
64 2-(2-(phenylsulfonyl)ethylthio)-N-(4-(trifluoromethylthio)benzyl)-nicotinamide
65 2-(2-(phenylsulfonyl)ethylthio)-N-(3-tolylmethyl)nicotinamide
66 (R)—N-(1-cyclohexylethyl)-2-(2-(phenylsulfonyl)ethylthio)nicotinamide
67 N-(1-(3,4-dimethylphenyl)ethyl)-2-(2-(phenylsulfonyl)ethylthio)-nicotinamide
68 N-(1-thiophen-2-ylethyl)-2-(2-(phenylsulfonyl)ethylthio)nicotinamide
69 N-(1-(3,5-dimethylphenyl)methyl)-2-(2-(phenylsulfonyl)ethylthio)-nicotinamide
70 N-(cyclohexylmethyl)-2-(2-(3-trifluoromethylphenylsulfonyl)ethylthio)-nicotinamide
71 (S)—N-(1-cyclohexylethyl)-2-(2-(phenylsulfonyl)ethylthio)nicotinamide
72 N-(1-(3,5-dimethylphenyl)ethyl)-2-(2-(phenylsulfonyl)ethylthio)-nicotinamide
73 N-(thiophen-2-ylmethyl)-2-(2-(3-(trifluoromethyl)phenylthio)ethylthio)-nicotinamide
74 N-(cyclopentylmethyl)-2-(2-(phenylsulfonyl)ethylthio)nicotinamide
75 N-(cyclobutylmethyl)-2-(2-(phenylsulfonyl)ethylthio)nicotinamide
76 N-((1,4-dioxan-2-yl)methyl)-2-(2-(phenylsulfonyl)ethylthio)nicotinamide
77 2-(2-(phenylsulfonyl)ethylthio)-N-(4-(pyridin-2-yloxy)benzyl)nicotinamide
78 N-(2-methylbutyl)-2-(2-(phenylsulfonyl)ethylthio)nicotinamide
79 N-(2-ethylbutyl)-2-(2-(phenylsulfonyl)ethylthio)nicotinamide
80 N-(cyclopropylmethyl)-2-(2-(phenylsulfonyl)ethylthio)nicotinamide
81 N-(3-(2-methoxyethoxy)propyl)-2-(2-(phenylsulfonyl)ethylthio)nicotin-amide
82 2-(2-(phenylsulfonyl)ethylthio)-N-(1-(4-(trifluoromethylthio)phenyl)ethyl)-nicotinamide
83 N-(3-(1H-pyrazol-1-yl)benzyl)-2-(2-(phenylsulfonyl)ethylthio)nicotinamide
84 N-((2,3-dihydrobenzofuran-5-yl)methyl)-2-(2-(phenylsulfonyl)ethylthio)-nicotinamide
85 N-(4-phenoxybenzyl)-2-(2-(phenylsulfonyl)ethylthio)nicotinamide
86 N-(((1R,2S,5R)-6,6-dimethylbicyclo[3.1.1]heptan-2-yl)methyl)-2-(2-(phenylsulfonyl)ethylthio)nicotinamide
87 N-(thiophen-2-ylmethyl)-2-(2-(3-(trifluoromethyl)phenylsulfonyl)ethylthio)-nicotinamide
88 2-(2-(phenylsulfonyl)ethylthio)-N-(3-(trifluoromethyl)benzyl)nicotinamide
93 N-isobutyl-2-(2-(phenylsulfonyl)ethylthio)nicotinamide
94 2-[2-(benzenesulfonyl)ethylthio]-N-(2-tetrahydropyranylmethyl)-nicotinamide
95 2-[2-(benzenesulfonyl)ethylthio]-N-[(5-methyl-2-thienyl)methyl]-nicotinamide
96 2-[2-(benzenesulfonyl)ethylthio]-N-[(4-methyl-2-thienyl)methyl]-nicotinamide
97 N-(1-adamantylmethyl)-2-[2-(benzenesulfonyl)ethylthio]-nicotinamide
98 2-[2-(benzenesulfonyl)ethylthio]-N-[(3-morpholinophenyl)methyl]-nicotinamide
99 2-[2-(4-chlorophenyl)sulfonylethylthio]-N-(2-thienylmethyl)-nicotinamide
100 2-[2-(4-fluorophenyl)sulfonylethylthio]-N-(2-thienylmethyl)-nicotinamide
101 N-(2-thienylmethyl)-2-[2-[3-(trifluoromethoxy)phenyl]sulfonylethylthio]-nicotinamide
102 N-(2-thienylmethyl)-2-[2-[4-(trifluoromethyl)phenyl]sulfonylethylthio]-nicotinamide
103 N-(2-thienylmethyl)-2-[2-[4-(trifluoromethoxy)phenyl]sulfonylethylthio]-nicotinamide
104 2-[2-(m-tolylsulfonyl)ethylthio]-N-(2-thienylmethyl)-nicotinamide
105 2-[2-(m-tolylthio)ethylthio]-N-(2-thienylmethyl)-nicotinamide
106 2-[2-(3-fluorophenyl)sulfonylethylthio]-N-(2-thienylmethyl)-nicotinamide
107 2-[2-(benzenesulfonyl)ethylthio]-N-(3,3-dimethylbutyl)-nicotinamide
108 2-[2-(benzenesulfonyl)ethylthio]-N-(2-benzothiophenylmethyl)-nicotinamide 109 2-[2-(phenylthio)ethylthio]-N-(2-thienylmethyl)-nicotinamide
110 2-[2-(benzenesulfinyl)ethylthio]-N-(2-thienylmethyl)-nicotinamide
111 2-(2-cyclohexylsulfonylethylthio)-N-(2-thienylmethyl)-nicotinamide
112 N-(2-thienylmethyl)-2-[2-[[2-(trifluoromethyl)phenyl]thio]ethylthio]-nicotinamide
113 N-(2-thienylmethyl)-2-[2-[2-(trifluoromethyl)phenyl]sulfinylethylthio]-nicotinamide
114 N-(2-thienylmethyl)-2-[2-[2-(trifluoromethyl)phenyl]sulfonylethylthio]-nicotinamide
115 2-[2-(benzenesulfonyl)ethylthio]-N-[(5-chloro-2-thienyl)methyl]-nicotinamide
116 2-[2-(2-fluorophenyl)sulfonylethylthio]-N-(2-thienylmethyl)-nicotinamide
117 2-[2-[3,5-bis(trifluoromethyl)phenyl]sulfonylethylthio]-N-(2-thienylmethyl)-nicotinamide
118 2-[2-(3-methoxyphenyl)sulfonylethylthio]-N-(2-thienylmethyl)-nicotinamide
119 2-[2-(4-methoxyphenyl)sulfonylethylthio]-N-(2-thienylmethyl)-nicotinamide
120 2-[2-(benzenesulfonyl)ethylthio]-N-(4-tetrahydrothiopyranylmethyl)-nicotinamide
121 2-[2-(4-ethylphenyl)sulfonylethylthio]-N-(2-thienylmethyl)-nicotinamide
122 N-(2-thienylmethyl)-2-[2-[[4-(trifluoromethyl)phenyl]thio]ethylthio]-nicotinamide
123 2-[2-(o-tolylthio)ethylthio]-N-(2-thienylmethyl)-nicotinamide
124 2-[2-[(3-fluorophenyl)thio]ethylthio]-N-(2-thienylmethyl)-nicotinamide
125 2-[2-[(3,4-difluorophenyl)thio]ethylthio]-N-(2-thienylmethyl)-nicotinamide
126 2-[2-[(2,4-difluorophenyl)thio]ethylthio]-N-(2-thienylmethyl)-nicotinamide
127 2-[2-(benzenesulfonyl)ethylthio]-N-[2-(2-thienyl)ethyl]-nicotinamide
128 2-[2-(benzenesulfonyl)ethylthio]-N-phenthyl-nicotinamide
129 2-[2-(benzenesulfonyl)ethylthio]-N-(3-phenylpropyl)-nicotinamide
130 2-[2-(3,4-difluorophenyl)sulfonylethylthio]-N-(2-thienylmethyl)-nicotinamide
131 2-[2-(2,4-difluorophenyl)sulfonylethylthio]-N-(2-thienylmethyl)-nicotinamide
132 2-[2-[(2-fluorophenyl)thio]ethylthio]-N-(2-thienylmethyl)-nicotinamide
133 2-[2-[(4-fluorophenyl)thio]ethylthio]-N-(2-thienylmethyl)-nicotinamide
134 2-[2-[(4-chlorophenyl)thio]ethylthio]-N-(2-thienylmethyl)-nicotinamide
135 2-[2-(p-tolylthio)ethylthio]-N-(2-thienylmethyl)-nicotinamide
136 2-[2-(benzenesulfonyl)ethylthio]-N-isopentyl-nicotinamide
137 2-[2-(benzenesulfonyl)ethylthio]-N-(2-cyclopropylethyl)-nicotinamide
138 2-[2-(benzenesulfonyl)ethylthio]-N-(2-cyclopentylethyl)-nicotinamide
139 N-(3,3-dimethylbutyl)-2-[2-[3-(trifluoromethyl)phenyl]sulfonylethylthio]-nicotinamide
140 N-(cyclopentylmethyl)-2-[2-[3-(trifluoromethyl)phenyl]sulfonylethylthio]-nicotinamide
141 2-[2-(benzenesulfonyl)ethylthio]-6-methyl-N-(2-thienylmethyl)-nicotinamide
142 2-[2-(benzenesulfonyl)ethylthio]-N-(2-thienylmethyl)-6-(trifluoromethyl)-nicotinamide
143 2-[2-(benzenesulfonyl)ethylthio]-6-fluoro-N-(2-thienylmethyl)-nicotinamide
144 2-[2-(benzenesulfonyl)ethylthio]-N-[(3-methylcyclohexyl)methyl]-nicotinamide
145 2-[2-(benzenesulfonyl)ethylthio]-N-(cycloheptylmethyl)-nicotinamide
146 2-[2-(benzenesulfonyl)ethylthio]-N-[(2-methylcyclohexyl)methyl]-nicotinamide
147 2-[2-(benzenesulfonyl)ethylthio]-N-[(4-methylcyclohexyl)methyl]-nicotinamide
148 2-[2-(benzenesulfonyl)ethylthio]-5-fluoro-N-(2-thienylmethyl)-nicotinamide
149 2-[2-(benzenesulfonyl)ethylthio]-5-methyl-N-(2-thienylmethyl)-nicotinamide
150 2-[2-(benzenesulfonyl)ethylthio]-N-(2-thienylmethyl)-5-(trifluoromethyl)-nicotinamide.

The substituted nicotinamide compounds according to the invention, and in each case the corresponding acids, bases, salts and solvates, are suitable as pharmaceutical active ingredients in medicaments.

The present invention therefore further provides a medicament comprising at least one substituted nicotinamide compound of the general formula I according to the invention, wherein n=0, 1 or 2
p=0 or 1
q=0 or 1,
$R^1$ denotes aryl or heteroaryl, unsubstituted or mono- or poly-substituted; $C_{1-6}$-alkyl, $C_{3-10}$-cycloalkyl or heterocyclyl, unsubstituted or mono- or poly-substituted;
$R^2$ denotes H; $C_{1-6}$-alkyl, unsubstituted or mono- or poly-substituted;
$R^3$ denotes aryl or heteroaryl, unsubstituted or mono- or poly-substituted; $C_{1-6}$-alkyl or $C_{3-10}$-cycloalkyl, in each case unsubstituted or mono- or poly-substituted;
$R^4$, $R^5$, $R^6$ and $R^7$ independently of one another each denote H or $C_{1-6}$-alkyl, unsubstituted or mono- or poly-substituted;
$R^8$, $R^9$ and $R^{10}$ independently of one another each denote H, F, Cl, Br, O—$C_{1-6}$-alkyl, $CF_3$, $OCF_3$, $SCF_3$, $C_{1-6}$-alkyl; and optionally one or more pharmaceutically acceptable auxiliary substances.

Preference is given to medicaments falling within the above-mentioned preferred ranges and combinations thereof.

Particular preference is given to pharmaceutical compositions medicaments selected from the following group consisting of:

89 2-(2-(phenylsulfonyl)ethylthio)-N-(thiophen-2-ylmethyl) nicotinamide
90 N-(pyridin-2-ylmethyl)-2-(2-(3-(trifluoromethyl)phenylsulfonyl)ethylthio)-nicotinamide
91 N-(pyridin-2-ylmethyl)-2-(2-(5-(trifluoromethyl)pyridin-2-ylsulfonyl)ethyl-thio)nicotinamide
92 N-(thiophen-2-ylmethyl)-2-(2-(5-(trifluoromethyl)pyridin-2-ylsulfonyl)ethyl-thio)nicotinamide.

These medicaments according to the invention are suitable for influencing KCNQ2/3 channels and exert an agonistic or antagonistic, in particular an agonistic, action. The medicaments of the invention are particularly suitable for the treatment of disorders or diseases which are at least partly mediated by KCNQ2/3 channels.

The medicament according to the invention is preferably suitable for the treatment of one or more diseases selected from the group consisting of pain, preferably pain selected from the group consisting of acute pain, chronic pain, neuropathic pain, muscular pain and inflammatory pain, migraine;

epilepsy, anxiety states and urinary incontinence. The medicaments according to the invention are particularly preferably suitable for the treatment of pain, very particularly preferably of chronic pain, neuropathic pain, inflammatory pain and muscular pain. The compounds according to the invention are further preferably suitable for the treatment of epilepsy.

The present invention also provides the use of at least one substituted nicotinamide compound according to the invention and optionally one or more pharmaceutically acceptable auxiliary substances in the preparation of a medicament and for the treatment of disorders or diseases which are at least partly mediated by KCNQ2/3 channels. In particular, one or more substituted nicotinamide compound according to the invention and optionally one or more pharmaceutically acceptable auxiliary substances may be used for the preparation of a medicament and for the treatment of pain, preferably of pain selected from the group consisting of acute pain, chronic pain, neuropathic pain, muscular pain and inflammatory pain; migraine; epilepsy, anxiety states and urinary incontinence. Particular preference is given to the use of at least one substituted nicotinamide compound according to the invention and optionally one or more pharmaceutically acceptable auxiliary substances in the preparation of a medicament and for the treatment of pain, very particularly preferably of chronic pain, neuropathic pain, inflammatory pain and muscular pain. Particular preference is further given to the use of at least one substituted nicotinamide compound according to the invention and optionally one or more pharmaceutically acceptable auxiliary substances in the preparation of a medicament for the treatment of epilepsy.

The effectiveness of the compounds and compositions of the present invention against pain can be shown, for example, in the Bennett or Chung model described hereinafter. The effectiveness against epilepsy can be shown, for example, in the DBA/2 mouse model (De Sarro et al., Naunyn-Schmiedeberg's Arch. Pharmacol. 2001, 363, 330-336).

The present invention also includes a process for preparing the substituted nicotinamide compounds according to the invention. The chemicals and reaction components employed in the reactions described above are commercially available or in each case can be prepared by conventional methods known to persons skilled in the art.

General Synthesis

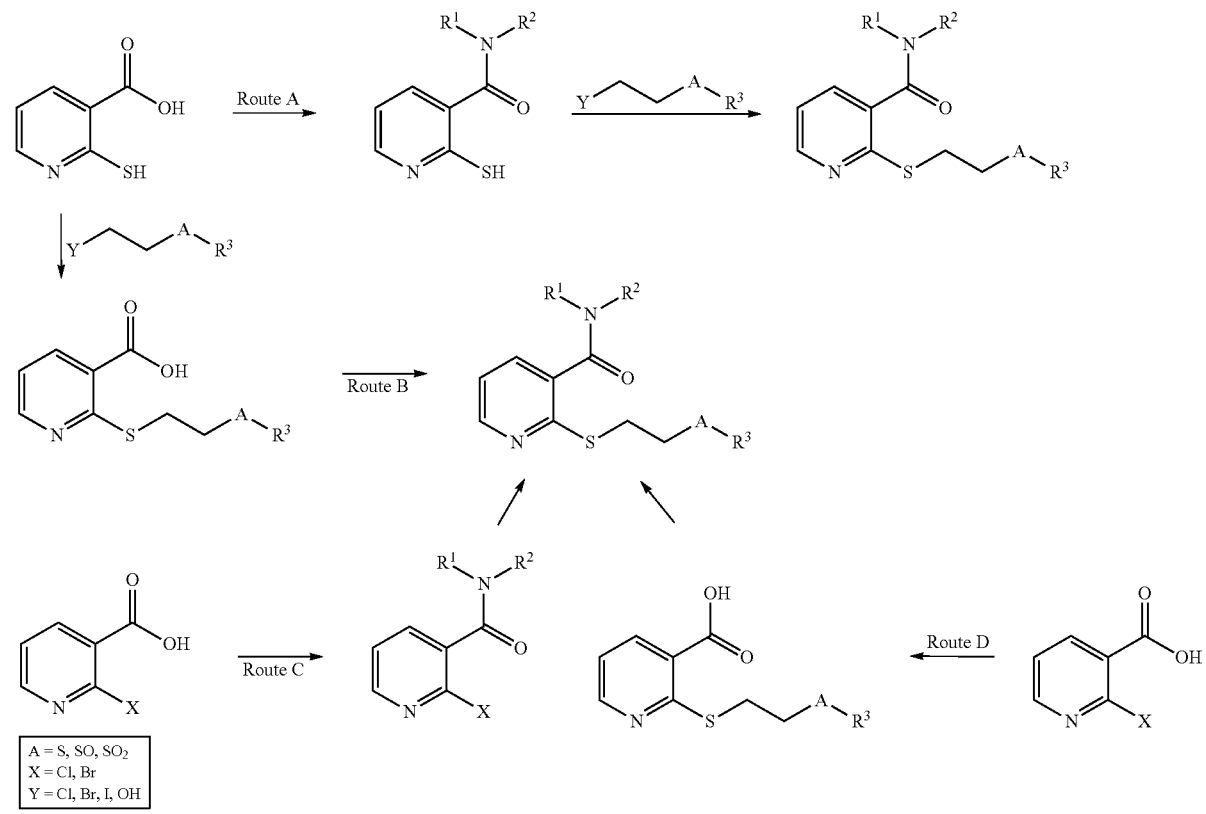

Route A (A=S, SO, $SO_2$)

The initial acylating reaction of amines with the aid of carboxylic acids, in this case mercaptonicotinic acid, using bases and optionally coupling reagents can be carried out in solvents, such as, for example, methanol, DMF or DCM. Examples of bases which can be used are sodium methanolate, triethylamine, diisopropylethylamine or N-methylmorpholine. Suitable coupling reagents are, for example, EDCI, HOBt, DCC, CDI, HBTU, DMAP or pentafluorophenyldiphenyl phosphinate. The reaction time can vary from 1 hour to 3 days. However, it is also possible first to convert the mercaptonicotinic acid into the carboxylic acid chloride. Suitable reagents for this purpose include, for example, $COCl_2$, $PCl_3$, $POCl_3$, $P_2O_5$, $SOCl_2$ or $SiCl_4$ in solvents such as, for example, pyridine, DCM, DMF or toluene.

For the subsequent thioether formation, it may be necessary to prepare the halogenated thioether Y—$CH_2$—$CH_2$-A-$R^3$ (where A=S). To this end, for example, a corresponding thiol can be reacted under UV irradiation with vinyl halides. Furthermore, the halogenated thioether Y—$CH_2$—$CH_2$-A-$R^3$ (where A=S) can be carried out, for example, by reaction of a corresponding thiol with a mixture of acetylene and bromine in carbon tetrachloride. A further method uses the reaction of 1,2-dihaloalkanes with a thiol in benzene, toluene or methanol in the presence of bases such as, for example, NaOH, KOH or sodium methanolate, optionally with the addition of hydrazine or tricaprylmethylammonium chloride.

The corresponding halogenated thioether Y—$CH_2$—$CH_2$-A-$R^3$ (where A=S) can optionally be oxidized to the corresponding sulfoxide Y—$CH_2$—$CH_2$-A-$R^3$ (where A=SO). This oxidation can be carried out with oxidizing agents such as, for example, $H_2O_2$, $NaIO_4$, $NaClO_2$, m-chloroperbenzoic acid or oxone in solvents such as, for example, glacial acetic acid, water, methanol, ethanol, 2-propanol, DCM or THF or in mixtures of these solvents.

The reaction of a corresponding halogenated thiol Y—$CH_2$—$CH_2$-A-$R^3$ (where A=S), sulfoxide Y—$CH_2$—$CH_2$-A-$R^3$ (where A=SO) or sulfone Y—$CH_2$—$CH_2$-A-$R^3$ (where A=$SO_2$) with the mercaptonicotinic acid amide can be carried out both with iodides, bromides or chlorides in the presence of bases, such as, for example, potassium carbonate, KOH, NaOH, triethylamine, diisopropylethylamine, sodium methanolate or ethanolate or sodium acetate, in solvents such as, for example, diethyl ether, THF, DMF, acetone, acetonitrile, DCM, water, ethanol or methanol.

The thioether can also be formed by reaction of the mercaptonicotin-amide with a corresponding alcohol HO—$CH_2$—$CH_2$-A-$R^3$ (where A=S, SO, $SO_2$) using reagents such as, for example, sulfuric acid, phosphoric acid, perchloric acid, acetic anhydride or zirconium tetrachloride. In addition to these acidic reagents, however, it is also possible to use bases, such as, for example, sodium hydride. However, (N-methyl-N-phenylamino)triphenylphosphonium iodide, phenyl methanesulfonate, hexamethylphosphoric acid triamide or 1-pentyl-3-methylimidazolium bromide are also suitable as further coupling reagents. The mentioned reagents can be used both individually and in combinations. Examples of suitable solvents include water, diethyl ether, acetic acid and DMF.

The corresponding alcohol HO—$CH_2$—$CH_2$-A-$R^3$ (where A=SO) is obtained by oxidation of the corresponding thioether HO—$CH_2$—$CH_2$-A-$R^3$ (where A=S) with oxidizing agents such as, for example, $H_2O_2$, $NaIO_4$, $NaClO_2$, m-chloroperbenzoic acid or oxone in solvents such as, for example, glacial acetic acid, water, methanol, ethanol, 2-propanol, DCM or THF or in mixtures of these solvents.

Route B (A=S, SO, $SO_2$)

The mercaptonicotinic acid thioether can be formed by reaction of the mercaptonicotinic acid with a corresponding alcohol HO—$CH_2$—$CH_2$-A-$R^3$ (where A=S, SO, $SO_2$) using reagents such as, for example, sulfuric acid, phosphoric acid, perchloric acid, acetic anhydride or zirconium tetrachloride. In addition to these acidic reagents, however, it is also possible to use bases, such as, for example, sodium hydride. However, (N-methyl-N-phenylamino)triphenyl-phosphonium iodide, phenyl methanesulfonate, hexamethylphosphoric acid triamide or 1-pentyl-3-methylimidazolium bromide are also suitable as further coupling reagents. The mentioned reagents can be used both individually and in combinations. Examples of suitable solvents include water, diethyl ether, acetic acid and DMF.

The reaction of a corresponding halogenated compound HO—$CH_2$—$CH_2$-A-$R^3$ (where A=S, SO, $SO_2$, Y=Cl, Br, I) with the mercaptonicotinic acid can be carried out both with iodides, bromides or chlorides in the presence of bases, such as, for example, potassium carbonate, KOH, NaOH, triethylamine, diisopropylethylamine, sodium methanolate or ethanolate or sodium acetate, in solvents such as, for example, diethyl ether, THF, DMF, acetone, acetonitrile, DCM, water, ethanol or methanol.

The subsequent acylation using bases and optionally coupling reagents can be carried out in solvents such as, for example, methanol, DMF or DCM. Examples of bases which can be used are sodium methanolate, triethylamine, diisopropylethylamine or N-methylmorpholine. Suitable coupling reagents are, for example, EDCI, HOBt, DCC, CDI, HBTU, DMAP or pentafluorophenyl-diphenyl phosphinate. The reaction time can vary from 1 hour to 3 days.

However, it is also possible first to convert the carboxylic acid into the carboxylic acid chloride. Suitable reagents for this purpose include, for example, $COCl_2$, $PCl_3$, $POCl_3$, $P_2O_5$, $SOCl_2$ or $SiCl_4$ in solvents such as, for example, pyridine, DCM, DMF or toluene.

Route C (A=S, $SO_2$)

The initial acylating reaction of amines with the aid of carboxylic acids, in this case the halogenated nicotinic acid, using bases and optionally coupling reagents can be carried out in solvents, such as, for example, methanol, DMF or DCM. Examples of bases which can be used are sodium methanolate, triethylamine, diisopropylethylamine or N-methylmorpholine. Suitable coupling reagents are, for example, EDCI, HOBt, DCC, CDI, HBTU, DMAP or pentafluorophenyldiphenyl phosphinate. The reaction time can vary from 1 hour to 3 days.

However, it is also possible first to convert the carboxylic acid into the carboxylic acid chloride. Suitable reagents for this purpose include, for example, $COCl_2$, $PCl_3$, $POCl_3$, $P_2O_5$, $SOCl_2$ or $SiCl_4$ in solvents such as, for example, pyridine, DCM, DMF or toluene.

For the subsequent substitution reaction with the corresponding thiols HS—$CH_2$—$CH_2$-A-$R^3$ or thiolates —S—$CH_2$—$CH_2$-A-$R^3$, both chlorine derivatives and bromine derivatives (X=Cl, Br) of the nicotinic acid are suitable. The substitution can be used in solvents such as, for example, methanol, ethanol, 2-propanol, 2-methyl-2-propanol, benzene, toluene, THF, dioxane, acetonitrile, chloroform, DMF, DMSO or mixtures of the solvents.

Suitable bases for the production of the thiolate include, for example, KOH, NaOH, potassium carbonate, sodium methanolate, sodium ethanolate, potassium tert-butoxide, triethylamine, sodium hydride but also, for example, sodium. As additives there can be used, for example, compounds such as sodium iodide, tetrabutylammonium bromide, chloride or hydrogen sulfate, or HMPT.

Route D (A=S, $SO_2$)

Both the chlorine derivatives and bromine derivatives of the nicotinic acid (X=Cl, Br) are suitable for the substitution reaction with thiols HS—$CH_2$—$CH_2$-A-$R^3$ or thiolates —S—$CH_2$—$CH_2$-A-$R^3$. The substitution can be used in solvents such as, for example, methanol, ethanol, 2-propanol, 2-methyl-2-propanol, benzene, toluene, THF, dioxane, acetonitrile, chloroform, DMF, DMSO or mixtures of the solvents.

Suitable bases for the production of the thiolate include, for example, KOH, NaOH, potassium carbonate, sodium methanolate, sodium ethanolate, potassium tert-butoxide, triethylamine, sodium hydride but also, for example, sodium. As additives there can be used, for example, compounds such as sodium iodide, tetrabutylammonium bromide, chloride or hydrogen sulfate, or HMPT.

The subsequent acylation reaction of amines with the aid of carboxylic acids using bases and optionally coupling reagents can be carried out in solvents such as, for example, methanol, DMF or DCM. Examples of bases which can be used are sodium methanolate, triethylamine, diisopropylethyl-amine or N-methylmorpholine. Suitable coupling reagents include, for example, EDCI, HOBt, DCC, CDI, HBTU, DMAP or pentafluorophenyldiphenyl phosphinate. The reaction time can vary from 1 hour to 3 days.

However, it is also possible first to convert the carboxylic acid into the carboxylic acid chloride. Suitable reagents for this purpose include, for example, $COCl_2$, $PCl_3$, $POCl_3$, $P_2O_5$, $SOCl_2$ or $SiCl_4$ in solvents such as, for example, pyridine, DCM, DMF or toluene.

The reactions described above can furthermore in each case be carried out under conventional conditions familiar to the person skilled in the art, for example in respect of pressure, temperature, protecting gas atmosphere or sequence of addition of the components. The optimum process procedure under the particular conditions can optionally be determined by persons skilled in the art by simple preliminary experiments.

All the process steps described above and in each case also the purification and/or isolation of intermediates or end products can be carried out in part or entirely under an inert gas atmosphere, preferably under a nitrogen atmosphere or argon atmosphere.

The substituted nicotinamide compounds according to the invention can be isolated both in the form of their free bases and their free acids and in each case also in the form of corresponding salts, in particular physiologically acceptable salts. The free bases of the particular substituted nicotinamide compounds according to the invention can be converted into the corresponding salts, preferably physiologically acceptable salts, for example, by reaction with an inorganic or organic acid, preferably with hydrochloric acid, hydrobromic acid, sulfuric acid, phosphoric acid, methanesulfonic acid, p-toluenesulfonic acid, carbonic acid, formic acid, acetic acid, oxalic acid, maleic acid, malic acid, succinic acid, tartaric acid, mandelic acid, fumaric acid, lactic acid, citric acid, glutamic acid or aspartic acid. The free bases of the particular substituted nicotinamide compounds according to the invention can likewise be converted into the corresponding physiologically acceptable salts with the free acid or a salt of a sugar substitute, such as, for example, saccharin, cyclamate or acesulfame.

Correspondingly, the free acids of the substituted nicotinamide compounds according to the invention can be converted into the corresponding physiologically acceptable salts by reaction with a suitable base. Examples which may be mentioned are the alkali metal salts, alkaline earth metal salts or ammonium salts $[NH_xR_{4-x}]^+$, wherein x=0, 1, 2, 3 or 4 and R represents a linear or branched $C_{1-4}$-alkyl radical.

The substituted nicotinamide compounds according to the invention can optionally, like the corresponding acids, the corresponding bases or salts of these compounds, also be obtained in the form of their solvates, preferably in the form of their hydrates, by conventional methods known to the person skilled in the art.

If the substituted nicotinamide compounds according to the invention contain one or more chiral carbon atoms, they may be obtained after their preparation in the form of a mixture of their stereoisomers, preferably in the form of their racemates or other mixtures of their various enantiomers and/or diastereoisomers. These can be separated by conventional processes known to the person skilled in the art and optionally isolated. Examples which may be mentioned are chromatographic separation processes, in particular liquid chromatography processes under normal pressure or under elevated pressure, preferably MPLC and HPLC processes, and processes of fractional crystallization. In this context, individual enantiomers, e.g. diastereoisomeric salts formed by HPLC on a chiral stationary phase or by crystallization with chiral acids, for example (+)-tartaric acid, (−)-tartaric acid or (+)-10-camphorsulfonic acid, can in particular be separated from one another.

The medicament according to the invention can be in a liquid, semi-solid or solid medicament form, for example in the form of injection solutions, drops, juices, syrups, sprays, suspensions, tablets, patches, capsules, plasters, suppositories, ointments, creams, lotions, gels, emulsions, aerosols or in multiparticulate form, for example in the form of pellets or granules, optionally pressed to tablets, filled into capsules or suspended in a liquid, and can also be administered as such. In addition to at least one substituted nicotinamide compound according to the invention, the medicament according to the invention conventionally comprises further physiologically acceptable pharmaceutical auxiliary substances, which can preferably be selected from the group consisting of carriers, fillers, solvents, diluents, surface-active substances, colourings, preservatives, disintegrating agents, slip agents, lubricants, flavourings and binders.

The choice of the physiologically acceptable auxiliary substances and the amounts thereof to be employed depends on whether the medicament is to be administered orally, subcutaneously, parenterally, intravenously, intra-peritoneally, intradermally, intramuscularly, intranasally, buccally, rectally or locally, for example to infections on the skin, the mucous membranes and on the eyes. Formulations in the form of tablets, coated tablets, capsules, granules, pellets, drops, juices and syrups are preferably suitable for oral administration, and solutions, suspensions, easily reconstitutable dry formulations and sprays are suitable for parenteral, topical and inhalatory administration.

The substituted nicotinamide compounds employed in the medicament according to the invention can be in a depot, in dissolved form or in a plaster, optionally with the addition of agents which promote penetration through the skin, as suitable formulations for percutaneous administration.

Formulation forms which can be used orally or percutaneously can also release the particular substituted nicotinamide compound according to the invention in a delayed manner.

The preparation of the medicaments according to the invention is carried out with the aid of conventional means, devices, methods and processes known in the art, such as are described, for example, in "Remingtons Pharmaceutical Sciences", editor A. R. Gennaro, 17th edition, Mack Publishing Company, Easton, Pa., 1985, in particular in part 8, chapters 76 to 93.

The amount of the particular substituted nicotinamide compound according to the invention to be administered to the patient can vary and depends, for example, on the weight or age of the patient and on the mode of administration, the indication and the severity of the disease. From 0.005 to 100 mg/kg, preferably from 0.05 to 75 mg/kg of body weight of the patient of at least one such compound according to the invention are typically administered.

The invention is described in further detail hereinafter with reference to some illustrative examples, which serve to illustrate the invention and are not to be interpreted as limiting.

Synthesis of the Example Compounds

Description of the Synthesis of the Precursors

Synthesis of
2-mercapto-N-(thiophen-2-ylmethyl)nicotinamide
(precursor V1)

A suspension of 8.0 g (51.5 mmol) of 2-mercaptonicotinic acid, 5.8 g (51.5 mmol) of 2-(aminomethyl)-thiophene and 3.5 g (25.8 mmol) of phosphorus trichloride in chlorobenzene (260 ml) was heated for 3 h under reflux (145° C.). When the reaction solution had cooled to 60° C., filtration with suction was carried out at that temperature. The solid obtained was taken up in a DCM/MeOH mixture (3:1, vv, 300 ml) and washed with water (2×50 ml). The organic phase was dried over MgSO$_4$, filtered and concentrated in vacuo. Crystallization of the residue from ethyl acetate yielded 3.1 g (12.4 mmol, 24%) of 2-mercapto-N-(thiophen-2-ylmethyl)nicotinamide.

1H NMR (400 MHz, DMSO-d$_6$) d ppm 4.73 (d, J=5.52 Hz, 2H) 6.97 (dd, J=5.02, 3.51 Hz, 1H) 7.01-7.11 (m, 2H) 7.41 (dd, J=5.27, 1.25 Hz, 1H) 7.98 (td, J=6.27, 2.01 Hz, 1H) 8.54 (dd, J=7.53, 2.01 Hz, 1H) 11.28 (t, J=5.52 Hz, 1H) 14.06 (br.s., 1H)

Precursors V2 and V3:

Synthesis of (2-bromoethyl)(cyclohexyl)sulfane (precursor V2)

19.4 ml (225.0 mmol) of 1,2-dibromoethane and 4.1 g (30.0 mmol) of K$_2$CO$_3$ were added to a solution of 3.7 ml (30.0 mmol) of cyclohexanethiol in DMF (46 ml). After 2 hours of stirring at RT, the mixture was diluted with diethyl ether (200 ml) and washed with saturated aqueous NaCl solution. The organic phase was dried over MgSO$_4$, filtered and concentrated in vacuo. The resulting 6.1 g of crude product (2-bromoethyl)(cyclohexyl)sulfane were used for the further reaction without being purified further.

Synthesis of (2-bromoethyl)(3-(trifluoromethyl)phenyl)sulfane (precursor V3)

According to the process described for V2, 10.5 g (58.9 mmol) of 3-trifluoromethyl-thiophenol were converted into 19.3 g of crude product (2-bromoethyl)(3-(trifluoromethyl)phenyl)sulfane, which was used for the further reaction without being purified further.

Synthesis of 2-chloro-6-methyl-N-(thiophen-2-ylmethyl)nicotinamide (precursor V4)

2.67 g (7.0 mmol) of HATU and 4.0 ml (23.2 mmol) of DIPEA were added at 0° C. to a solution of 1.0 g (5.8 mmol) of 2-chloro-6-methyl-nicotinic acid in DMF (20 ml), and the mixture was stirred for 20 min at 0° C. At that temperature, 656 mg (5.8 mmol) of thiophen-2-ylmethylamine were added. Stirring was then carried out for 16 h at RT. The mixture was then diluted with EA and washed in succession with sat. aq. NaHCO$_3$ solution and brine. The organic phase was dried over Na$_2$SO$_4$, filtered and concentrated in vacuo. CC (hexane/EA 4:1) of the residue yielded 966 mg (3.6 mmol, 63%) of 2-chloro-6-methyl-N-(thiophen-2-ylmethyl)nicotinamide.

Synthesis of (2-chloroethyl)(3,4-difluorophenyl)sulfane (precursor V9)

5.7 ml (68.4 mmol) of 1-bromo-2-chloroethane and 1.9 g (13.7 mmol) of K$_2$CO$_3$ were added to a solution of 2.0 g (13.7 mmol) of 3,4-difluorothiophenol in DMF (20 ml). Stirring was then carried out for 5 h at 60° C. and for 16 h at RT. The mixture was then diluted with EA (50 ml) and washed in succession with 1 M aq. Na$_2$CO$_3$ solution and brine. The organic phase was dried over MgSO$_4$, filtered and concentrated in vacuo. There were obtained as residue 2.7 g (12.9 mmol, 95%) of (2-chloroethyl)-(3,4-difluorophenyl)sulfane, which was reacted further without additional purification.

Synthesis of 4-(2-chloroethylsulfonyl)-1,2-difluorobenzene (precursor V10)

A solution of 3.06 g (12.5 mmol) of m-chloroperbenzoic acid in DCM (10 ml) was added dropwise at 5-10° C. to a solution of 1.04 g (5.0 mmol) of (2-chloroethyl)-(3,4-difluorophenyl)sulfane in DCM (10 ml). Stirring was then carried out for 150 min at 10° C. The mixture was then washed in each case twice with 1 M aq. NaHCO$_3$ solution and with sat. aq. Na$_2$SO$_3$ solution. The organic phase was dried over MgSO$_4$, filtered and concentrated in vacuo. There were obtained as residue 1.2 g (4.94 mmol, 99%) of 4-(2-chloroethylsulfonyl)-1,2-difluorobenzene, which was reacted further without additional purification.

Synthesis of (2-chloroethylsulfinyl)benzene (precursor V11)

A solution of 1.67 g (7.5 mmol) of m-chloroperbenzoic acid in DCM (10 ml) was added dropwise at 5-10° C. to a solution of 1.30 g (7.5 mmol) of (2-chloroethylsulfinyl)benzene in DCM (18 ml). Stirring was then carried out for 120 min at 10° C. The mixture was then washed in each case twice with 1 M aq. NaHCO$_3$ solution and once with brine. The organic phase was dried over MgSO$_4$, filtered and concentrated in vacuo. There were obtained as residue 1.34 g (7.1 mmol, 95%) of (2-chloroethylsulfinyl)benzene, which was reacted further without additional purification.

Synthesis of 1-(2-chloroethylsulfonyl)-4-ethylbenzene (precursor V12)

A solution of 1.0 ml (14.0 mmol) of thionyl chloride in toluene (15 ml) was added dropwise, while cooling with ice, to a solution of 1.0 g (4.67 mmol) of 2-(4-ethylphenylsulfonyl)-ethanol and 56 µl (0.70 mmol) of pyridine in toluene (20 ml). The mixture was then heated for 3 h under reflux. Quenching with ice and water was then carried out. The phases were separated and the aqueous phase was extracted twice with DCM. The combined organic phases were dried over MgSO$_4$, filtered and concentrated in vacuo. There were obtained as crude product 1.19 g of slightly impure 1-(2-chloroethylsulfonyl)-4-ethylbenzene, which was reacted further without additional purification.

Further precursors were prepared analogously to the described processes. Table T1 summarizes which precursors were prepared analogously to which process. It will be clear to the person skilled in the art which starting materials were used in each case.

TABLE T1

| Precursor | Name | Synthesis analogous to precursor |
|---|---|---|
| V5 | 2,6-difluoro-N-(thiophen-2-ylmethyl)-nicotinamide | V4 |
| V6 | 2-chloro-N-(thiophen-2-ylmethyl)-6-(trifluoromethyl)nicotinamide | V4 |
| V7 | 2-chloro-N-(thiophen-2-ylmethyl)-5-(trifluoromethyl)nicotinamide | V4 |

TABLE T1-continued

| Precursor | Name | Synthesis analogous to precursor |
|---|---|---|
| V8 | 2-chloro-5-fluoro-N-(thiophen-2-ylmethyl)nicotinamide | V4 |
| V13 | (2-chloroethyl)(4-fluorophenyl)sulfane | V9 |
| V14 | (2-chloroethyl)(2-trifluoromethylphenyl)sulfane | V9 |
| V15 | (2-chloroethyl)(3-trifluoromethylphenyl)sulfane | V9 |
| V16 | (2-chloroethyl)(4-trifluoromethylphenyl)sulfane | V9 |
| V17 | (2-chloroethyl)(3-trifluoromethoxyphenyl)sulfane | V9 |
| V18 | (2-chloroethyl)(4-trifluoromethoxyphenyl)sulfane | V9 |
| V19 | (2-chloroethyl)(2-methylphenyl)sulfane | V9 |
| V20 | (2-chloroethyl)(3-methylphenyl)sulfane | V9 |
| V21 | (2-chloroethyl)(2,4-difluorophenyl)sulfane | V9 |
| V22 | 1-(2-chloroethylsulfinyl)-3-(trifluoromethoxy)benzene | V11 |
| V23 | 1-(2-chloroethylsulfonyl)-2-fluorobenzene | V12 |
| V24 | 1-(2-chloroethylsulfonyl)-2-trifluoromethylbenzene | V10 |
| V25 | 1-(2-chloroethylsulfonyl)-4-trifluoromethylbenzene | V10 |
| V26 | 1-(2-chloroethylsulfonyl)-3-trifluoromethoxybenzene | V10 |
| V27 | 1-(2-chloroethylsulfonyl)-4-trifluoromethoxybenzene | V10 |
| V28 | 1-(2-chloroethylsulfonyl)-3-methylbenzene | V10 |
| V29 | 1-(2-chloroethylsulfonyl)-3-methoxybenzene | V12 |
| V30 | 1-(2-chloroethylsulfonyl)-4-methoxybenzene | V12 |
| V31 | 1-(2-chloroethylsulfonyl)-2,4-difluorobenzene | V10 |
| V32 | 1-(2-chloroethylsulfonyl)-3,5-ditrifluoromethylbenzene | V12 |

Amines Used (Table T2)

The following amines were used for the synthesis of the examples:

TABLE T2

| | |
|---|---|
| A01 | Phenylmethanamine |
| A02 | N-methyl-1-phenylmethanamine |
| A03 | pyridin-2-ylmethanamine |
| A04 | pyridin-4-ylmethanamine |
| A05 | thiophen-2-ylmethanamine |
| A06 | 2-(3-fluorophenyl)ethanamine |
| A07 | N-methyl-1-m-tolylmethanamine |
| A08 | furan-2-ylmethanamine |
| A09 | p-tolylmethanamine |
| A10 | (2-(trifluoromethyl)phenyl)methanamine |
| A11 | pyridin-3-ylmethanamine |
| A12 | (3,5-difluorophenyl)methanamine |
| A13 | N-methyl-2-phenylethanamine |
| A14 | 1-(3-methoxyphenyl)-N-methylmethanamine |
| A15 | (2-fluorophenyl)methanamine |
| A16 | m-tolylmethanamine |
| A17 | (3,4-difluorophenyl)methanamine |
| A18 | 1-(3-bromophenyl)-N-methylmethanamine |
| A19 | (2-methoxyphenyl)methanamine |
| A20 | (3-fluorophenyl)methanamine |
| A21 | 1-(furan-2-yl)-N-methylmethanamine |
| A22 | (4-methoxyphenyl)methanamine |
| A23 | (2-chlorophenyl)methanamine |
| A24 | (3,4-dichlorophenyl)methanamine |
| A25 | (4-fluorophenyl)methanamine |
| A26 | 2-(2-methoxyphenyl)ethanamine |
| A27 | (2,6-difluorophenyl)methanamine |
| A28 | o-tolylmethanamine |
| A29 | (3,5-dimethoxyphenyl)methanamine |
| A30 | (3-chlorophenyl)methanamine |
| A31 | (2,4-dichlorophenyl)methanamine |
| A32 | (3-(trifluoromethyl)phenyl)methanamine |
| A43 | (5-methylfuran-2-yl)methanamine |
| A44 | (4-chlorophenyl)methanamine |
| A45 | (2,3-dichlorophenyl)methanamine |
| A55 | 1-(4-bromophenyl)-N-methylmethanamine |
| A64 | 1-(1,3-dioxolan-2-yl)-N-methylmethanamine |
| A66 | Cyclopentylmethanamine |
| A67 | Cyclobutylmethanamine |
| A68 | (1,4-dioxan-2-yl)methanamine |
| A69 | (4-(pyridin-2-yloxy)phenyl)methanamine |
| A70 | 2-methylbutan-1-amine |
| A71 | 2-ethylbutan-1-amine |
| A72 | 2-methylpropan-1-amine |
| A73 | Cyclopropylmethanamine |
| A74 | 3-(2-methoxyethoxy)propan-1-amine |
| A75 | 1-(3,4-dimethylphenyl)ethanamine |
| A76 | Cyclohexylmethanamine |
| A77 | Methanamine |
| A78 | 1-(3-(trifluoromethyl)phenyl)ethanamine |
| A79 | 2-cyclohexylethanamine |
| A80 | 2,2-dimethylpropan-1-amine |
| A81 | (tetrahydro-2H-pyran-4-yl)methanamine |
| A82 | (4-(trifluoromethylthio)phenyl)methanamine |
| A83 | (S)-1-cyclohexylethanamine |
| A84 | 1-(3,5-dimethylphenyl)ethanamine |
| A85 | 1-(thiophen-2-yl)ethanamine |
| A86 | (3,5-dimethylphenyl)methanamine |
| A87 | (R)-1-cyclohexylethanamine |
| A88 | 3-(1H-pyrazol-1-yl)phenyl)methanamine |
| A89 | (2,3-dihydrobenzofuran-5-yl)methanamine |
| A90 | (4-phenoxyphenyl)methanamine |
| A91 | 6,6-dimethylbicyclo[3.1.1]heptan-2-yl)methanamine |
| A92 | 1-(4-(trifluoromethylthio)phenyl)ethanamine |
| A93 | (tetrahydro-2H-pyran-2-yl)methanamine |
| A94 | (5-methylthiophen-2-yl)methanamine |
| A95 | (4-methylthiophen-2-yl)methanamine |
| A96 | 1-adamantylmethanamine |
| A97 | (3-morpholinophenyl)methanamine |
| A98 | 3,3-dimethylbutan-1-amine |
| A99 | benzo[b]thiophen-2-ylmethanamine |
| A100 | (5-chlorothiophen-2-yl)methanamine |
| A101 | (tetrahydro-2H-thiopyran-4-yl)methanamine |
| A102 | 2-(thiophen-2-yl)ethanamine |
| A103 | 2-phenylethanamine |
| A104 | 3-phenylpropan-1-amine |
| A105 | 3-methylbutan-1-amine |
| A106 | 2-cyclopropylethanamine |
| A107 | 2-cyclopentylethanamine |
| A108 | Cycloheptylmethanamine |
| A109 | (2-methylcyclohexyl)methanamine |
| A110 | (4-methylcyclohexyl)methanamine |

The mentioned amines are either commercially available from suppliers such as ABCR, ACBBlocks, Acros, Aldrich, Array Biopharma, BASF, Fulcrum Scientific, Indofine, Interchim, Lancaster, Matrix, Maybridge, Rare Chemicals or Synchem or were synthesized, as in the case of A75, A82, A84 and A92.

Synthesis of 1-(3,4-dimethylphenyl)ethylamine (A75)

16.4 ml (150.0 mmol) of tetrapropyl orthotitanate were added to a solution of 4.46 g (30.0 mmol) of 3,4-dimethylacetophenone in a 2 M ethanolic ammonia solution (75 ml), and the mixture was stirred for 6 hours at RT. 1.7 g (45.0 mmol) of sodium borohydride were then added, and stirring was continued for a further 16 hours at RT. Thereafter, the reaction solution was poured into a saturated aqueous ammonia solution (75 ml). The precipitate that formed was filtered off with suction, and then washing with ethyl acetate was carried out. The aqueous filtrate was concentrated in vacuo, followed by extraction twice with ethyl acetate. The combined ethyl acetate phases were extracted three times with 2 M hydrochloric acid. The combined aqueous phases were adjusted to pH 11 with a 2 M aq. NaOH solution and then extracted three times with ethyl acetate. The combined organic phases were dried over MgSO$_4$, filtered and concentrated in vacuo. CC (ethyl acetate/MeOH 9:1) yielded 799 mg (5.4 mmol, 18%) of 1-(3,4-dimethylphenyl)ethylamine.

1H NMR (400 MHz, DMSO-d$_6$) d ppm 1.20 (d, J=6.6 Hz, 3H) 2.17 (s, 3H) 2.19 (s, 3H) 3.89 (q, J=6.6 Hz, 1H) 6.99-7.07 (m, 2H) 7.08-7.15 (m, 1H)

Synthesis of 4-(trifluoromethylthio)phenyl)methylamine (A82)

According to the process described for precursor A75, 5.0 g (24.2 mmol) of 4-(trifluoromethylthio)-benzaldehyde were converted into 64 mg (0.31 mmol, 1%) of 4-(trifluoromethylthio)phenyl)methylamine.

1H NMR (400 MHz, DMSO-d$_6$) d ppm 3.77 (s, 2H) 7.50 (d, J=8.03 Hz, 2H) 7.65 (d, J=8.03 Hz, 2H)

Synthesis of 1-(3,5-dimethylphenyl)ethylamine (A84)

According to the process described for precursor A75, 2.17 g (14.6 mmol) of 3,5-dimethylacetophenone were converted into 1.08 g (7.2 mmol, 50%) of 1-(3,5-dimethylphenyl)ethylamine.

1H NMR (400 MHz, DMSO-d$_6$) d ppm 1.20 (d, J=7.0 Hz, 3H) 2.23 (s, 6H), 3.88 (q, J=7.0 Hz, 1H) 6.77-6.83 (m, 1H) 6.91-7.00 (m, 2H)

Synthesis of 1-(4-(trifluoromethylthio)phenyl)ethanamine (A92)

According to the process described for precursor A75, 4.4 g (20.0 mmol) of 4'-(trifluoromethylthio)acetophenone were converted into 1.78 g (8.0 mmol, 40%) of 1-(4-(trifluoromethylthio)phenyl)ethanamine.

1H NMR (400 MHz, DMSO-d$_6$) d ppm 1.24 (d, J=6.6 Hz, 3H) 4.03 (q, J=6.6 Hz, 1H) 7.54 (d, J=8.53 Hz, 2H) 7.64 (d, J=8.03 Hz, 2H)

Acids Used 2-(2-(Phenylsulfonyl)ethylthio)nicotinic acid S1 is commercially available from the suppliers Alfa Aesar and ABCR.

Synthesis of 2-(2-tosylethylthio)nicotinic acid (acid S2)

A solution of 7.3 g (47 mmol) of 2-mercaptonicotinic acid and 9.6 g (48 mmol) of 2-(p-toluenesulfonyl)-ethanol was dissolved in DMF (80 ml). 0.5 ml of conc. H$_2$SO$_4$ was then carefully added dropwise, and stirring was carried out overnight under reflux. The reaction mixture was concentrated using a Genevac (EZ2). The residue was dissolved in acetonitrile and the solid was separated off. The mother liquor was concentrated, and MeOH was added. The resulting solid was filtered off and dried. 2.35 g (7 mmol, 14.8%) of 2-(2-tosylethylthio)nicotinic acid were obtained as solid.

1H NMR (400 MHz, CDCl$_3$) d ppm 2.48 (s, 3H) 3.31-3.44 (m, 2H) 3.48-3.59 (m, 2H) 7.09 (dd, J=7.78, 4.77 Hz, 1H) 7.40 (d, J=8.03 Hz, 2H) 7.85 (d, J=8.53 Hz, 2H) 8.27 (dd, J=7.78, 1.76 Hz, 1H) 8.40 (dd, J=4.52, 2.01 Hz, 1H)

Synthesis of 2-(2-(3-(trifluoromethyl)phenylsulfonyl)ethylthio)nicotinic acid (acid S3)

683 mg (4.92 mmol) of K$_2$CO$_3$ were added to a suspension of 349 mg (2.25 mmol) of 2-mercaptonicotinic acid in DMF (5 ml), and the mixture was stirred for 30 min at RT. 614 mg (2.25 mmol) of 2-chloroethyl-(3-(trifluoromethyl)phenyl) sulfone were then added, and stirring was continued for a further 72 h at RT. The reaction solution was concentrated in vacuo, the residue obtained was taken up in ethyl acetate, and water was added. The pH was adjusted to 3 with 2 M hydrochloric acid, and the phases were separated. The aqueous phase was extracted with ethyl acetate. The combined organic phases were dried over MgSO$_4$, filtered and concentrated in vacuo. 778 mg (1.99 mmol, 88%) of 2-(2-(3-(trifluoromethyl)phenylsulfonyl)ethylthio)nicotinic acid were obtained as residue.

1H NMR (400 MHz, DMSO-d$_6$) d ppm 3.20-3.29 (m, 2H) 3.72-3.86 (m, 2H) 7.23 (dd, J=7.78, 4.77 Hz, 1H) 7.96 (t, J=8.03 Hz, 1H) 8.15-8.22 (m, 2H) 8.23-8.32 (m, 2H) 8.34 (dd, J=4.77, 1.76 Hz, 1H)

Synthesis of 5-methyl-2-(2-(phenylsulfonyl)ethylthio)nicotinic acid (acid S4)

a) Synthesis of 2-mercapto-5-methylnicotinenitrile

A catalytic amount (16 μl) of 2-(dimethylamino)-ethanol was added to a solution of 1.7 g (20 mmol) of 2-cyanothioacetamide and 2.3 g (20.0 mmol) of 3-ethoxymethacrolein in EtOH (50 ml), and stirring was carried out for 24 h under reflux. The mixture was then largely concentrated in vacuo. The resulting precipitate was filtered off and washed with cold ethanol. There were thereby obtained 1.45 g (9.6 mmol, 48%) of 2-mercapto-5-methylnicotinenitrile, which was reacted further without additional purification.

b) Synthesis of 5-methyl-2-(2-(phenylsulfonyl)ethylthio)nicotinenitrile 1.9 g (14.0 mmol) of K$_2$CO$_3$ and 1.9 g (9.3 mmol) of (2-chloroethylsulfonyl)benzene were added to a solution of 1.40 g (9.3 mmol) of 2-mercapto-5-methylnicotinenitrile in acetone (30 ml), and stirring was then carried out for 16 h at 60° C. The mixture was then filtered off and the filtrate was concentrated in vacuo. The residue was taken up in water and extracted with EA (3×50 ml). The combined organic phases were washed with brine, dried over Na$_2$SO$_4$, filtered and concentrated in vacuo. CC (hexane/EA 4:1) of the residue yielded 1.41 g (4.4 mmol, 47%) of 5-methyl-2-(2-phenylsulfonyl)ethylthio)nicotinenitrile.

c) Synthesis of 5-methyl-2-(2-(phenylsulfonyl)ethylthio)nicotinic acid

A solution of 1.40 g (4.4 mmol) of 5-methyl-2-(2-(phenylsulfonyl)ethylthio)nicotinenitrile in 50% aq. sulfuric acid (10 ml) was heated for 4 days under reflux. The mixture was then poured onto ice-water and the resulting precipitate was filtered out. Washing with cold water was then carried out. There were obtained as residue 1.2 g (3.6 mmol, 81%) of 5-methyl-2-(2-(phenylsulfonyl)ethylthio)nicotinic acid, which was reacted further without additional purification.

DESCRIPTION OF THE SYNTHESIS OF THE EXAMPLES

Examples 1 to 52

100 μmol of the corresponding acid solution (0.05 M in DCM, 2 ml) were first placed at room temperature in a reaction vessel (Heidolph), 105 μmol of CDI solution (0.105 M in DCM, 1 ml) were added, and the mixture was shaken for 1 h at room temperature. 100 μmol of the corresponding amine (0.1 M in DCM, 1 ml) were then added at room temperature, and shaking was continued for a further 12 h at RT. When the reaction was complete, 3 ml of water were added, shaking was carried out for 15 min, and then the organic phase was separated. The solvent was removed using a Genevac and the products were purified by means of HPLC. The following compounds were synthesized according to this method (Table T3):

TABLE T3

| Example | Name | MS m/z [M + H]+ |
|---|---|---|
| 1 | 2-(2-(phenylsulfonyl)ethylthio)-N-(pyridin-2-ylmethyl)nicotinamide | 414.09 |
| 2 | 2-(2-(phenylsulfonyl)ethylthio)-N-(pyridin-4-ylmethyl)nicotinamide | 414.09 |
| 3 | N-(3-fluorophenethyl)-2-(2-(phenylsulfonyl)ethylthio)nicotinamide | 445.10 |
| 4 | N-methyl-N-(3-methylbenzyl)-2-(2-(phenylsulfonyl)ethylthio)nicotinamide | 441.12 |
| 5 | N-(4-methylbenzyl)-2-(2-(phenylsulfonyl)ethylthio)nicotinamide | 427.11 |
| 6 | 2-(2-(phenylsulfonyl)ethylthio)-N-(2-(trifluoromethyl)benzyl)nicotinamide | 481.08 |
| 7 | 2-(2-(phenylsulfonyl)ethylthio)-N-(pyridin-3-ylmethyl)nicotinamide | 414.09 |
| 8 | N-(3,5-difluorobenzyl)-2-(2-(phenylsulfonyl)ethylthio)nicotinamide | 449.07 |
| 9 | N-methyl-N-phenethyl-2-(2-(phenylsulfonyl)ethylthio)nicotinamide | 441.12 |
| 10 | N-(3-methoxybenzyl)-N-methyl-2-(2-(phenylsulfonyl)ethylthio)nicotinamide | 457.12 |
| 11 | N-(2-fluorobenzyl)-2-(2-(phenylsulfonyl)ethylthio)nicotinamide | 431.08 |
| 12 | N-(3,4-difluorobenzyl)-2-(2-(phenylsulfonyl)ethylthio)nicotinamide | 449.07 |
| 13 | N-(3-bromobenzyl)-N-methyl-2-(2-(phenylsulfonyl)ethylthio)nicotinamide | 505.02 |
| 14 | N-(2-methoxybenzyl)-2-(2-(phenylsulfonyl)ethylthio)nicotinamide | 443.10 |
| 15 | N-(3-fluorobenzyl)-2-(2-(phenylsulfonyl)ethylthio)nicotinamide | 431.08 |
| 16 | N-(furan-2-ylmethyl)-N-methyl-2-(2-(phenylsulfonyl)ethylthio)nicotinamide | 417.09 |
| 17 | N-(4-methoxybenzyl)-2-(2-(phenylsulfonyl)ethylthio)nicotinamide | 443.10 |
| 18 | N-(2-chlorobenzyl)-2-(2-(phenylsulfonyl)ethylthio)nicotinamide | 447.05 |
| 19 | N-(3,4-dichlorobenzyl)-2-(2-(phenylsulfonyl)ethylthio)nicotinamide | 481.01 |
| 20 | N-(4-fluorobenzyl)-2-(2-(phenylsulfonyl)ethylthio)nicotinamide | 431.08 |
| 21 | N-(2-methoxyphenethyl)-2-(2-(phenylsulfonyl)ethylthio)nicotinamide | 457.12 |
| 22 | N-(2,6-difluorobenzyl)-2-(2-(phenylsulfonyl)ethylthio)nicotinamide | 449.07 |
| 23 | N-(2-methylbenzyl)-2-(2-(phenylsulfonyl)ethylthio)nicotinamide | 427.11 |
| 24 | N-(3,5-dimethoxybenzyl)-2-(2-(phenylsulfonyl)ethylthio)-nicotinamide | 473.11 |
| 25 | N-(3-chlorobenzyl)-2-(2-(phenylsulfonyl)ethylthio)nicotinamide | 447.05 |
| 26 | N-(2,4-dichlorobenzyl)-2-(2-(phenylsulfonyl)ethylthio)nicotinamide | 481.01 |
| 29 | N-(4-chlorobenzyl)-2-(2-(phenylsulfonyl)ethylthio)nicotinamide | 447.05 |
| 30 | N-(2,3-dichlorobenzyl)-2-(2-(phenylsulfonyl)ethylthio)nicotinamide | 481.01 |
| 31 | N-(4-bromobenzyl)-N-methyl-2-(2-(phenylsulfonyl)ethylthio)nicotinamide | 505.02 |
| 32 | N-((1,3-dioxolan-2-yl)methyl)-N-methyl-2-(2-(phenylsulfonyl)ethylthio)nicotinamide | 423.10 |
| 33 | N-benzyl-N-methyl-2-(2-tosylethylthio)nicotinamide | 441.12 |
| 34 | N-(pyridin-2-ylmethyl)-2-(2-tosylethylthio)nicotinamide | 428.10 |
| 35 | N-(pyridin-4-ylmethyl)-2-(2-tosylethylthio)nicotinamide | 428.10 |
| 36 | N-(thiophen-2-ylmethyl)-2-(2-tosylethylthio)nicotinamide | 433.06 |
| 37 | N-(3-fluorophenethyl)-2-(2-tosylethylthio)nicotinamide | 459.11 |
| 38 | N-methyl-N-(3-methylbenzyl)-2-(2-tosylethylthio)nicotinamide | 455.14 |
| 39 | N-(furan-2-ylmethyl)-2-(2-tosylethylthio)nicotinamide | 417.09 |
| 40 | N-(pyridin-3-ylmethyl)-2-(2-tosylethylthio)nicotinamide | 428.10 |
| 41 | N-(3,5-difluorobenzyl)-2-(2-tosylethylthio)nicotinamide | 463.09 |
| 42 | N-(3-methoxybenzyl)-N-methyl-2-(2-tosylethylthio)nicotinamide | 471.13 |
| 43 | N-(2-fluorobenzyl)-2-(2-tosylethylthio)nicotinamide | 445.10 |
| 44 | N-(3-methylbenzyl)-2-(2-tosylethylthio)nicotinamide | 441.12 |
| 45 | N-(3,4-difluorobenzyl)-2-(2-tosylethylthio)nicotinamide | 463.09 |
| 46 | N-(3-bromobenzyl)-N-methyl-2-(2-tosylethylthio)nicotinamide | 519.03 |
| 47 | N-(4-methoxybenzyl)-2-(2-tosylethylthio)nicotinamide | 457.12 |
| 48 | N-(2-chlorobenzyl)-2-(2-tosylethylthio)nicotinamide | 461.07 |
| 49 | N-(4-fluorobenzyl)-2-(2-tosylethylthio)nicotinamide | 445.10 |
| 50 | N-(3,5-dimethoxybenzyl)-2-(2-tosylethylthio)nicotinamide | 487.13 |
| 51 | N-(3-chlorobenzyl)-2-(2-tosylethylthio)nicotinamide | 461.07 |
| 52 | 2-(2-tosylethylthio)-N-(3-(trifluoromethyl)benzyl)nicotinamide | 495.09 |

Example 54

Synthesis of N-benzyl-2-(2-(phenylsulfonyl)ethylthio)nicotinamide 132 mg (0.81 mmol) of CDI were added to a solution of 250 mg (0.77 mmol) of 2-(2-(phenylsulfonyl)ethylthio)nicotinic acid in DCM (6 ml), and the mixture was stirred for 1 h at RT. A solution of 82 mg (0.77 mmol) of benzylamine in DCM (6 ml) was then added, and stirring was continued for a further 16 hours at RT. The reaction solution was then washed in each case three times with a sat. aq. ammonium chloride solution and saturated aqueous $NaHCO_3$ solution. The organic phase was dried over $MgSO_4$, filtered and concentrated in vacuo. 266 mg (0.64 mmol, 83%) of N-benzyl-2-(2-(phenylsulfonyl)ethylthio)nicotinamide were obtained as residue.

1H NMR (600 MHz, DMSO-$d_6$) d ppm 3.16-3.26 (m, 2H) 3.56-3.68 (m, 2H) 4.38-4.49 (m, 2H) 7.19 (dd, J=7.55, 5.29 Hz, 1H) 7.22-7.28 (m, 1H) 7.29-7.37 (m, 4H) 7.70 (t, J=7.55 Hz, 2H) 7.79 (t, J=7.18 Hz, 1H) 7.88 (d, J=6.80 Hz, 1H) 7.95 (d, J=7.55 Hz, 2H) 8.31 (d, J=3.78 Hz, 1H) 9.02 (t, J=5.67 Hz, 1H)

Example 55

Synthesis of N-benzyl-N-methyl-2-(2-(phenylsulfonyl)ethylthio)-nicotinamide 132 mg (0.81 mmol) of CDI were added to a solution of 250 mg (0.77 mmol) of 2-(2-(phenylsulfonyl)ethylthio)nicotinic acid in DCM (6 ml), and the mixture was stirred for 1 hour at RT. A solution of 93 mg (0.77 mmol) of N-benzyl-N-methylamine in DCM (6 ml) was then added, and stirring was continued for a further 16 h at RT. The reaction solution was then washed in each case three times with sat. aq. ammonium chloride solution and saturated aqueous $NaHCO_3$ solution. The organic phase was dried over $MgSO_4$, filtered and concentrated in vacuo. CC with the residue (DCM→DCM/MeOH 99.5:0.5) yielded 152 mg (0.36 mmol, 46%) of N-benzyl-N-methyl-2-(2-(phenylsulfonyl)ethylthio)nicotinamide.

1H NMR (600 MHz, DMSO-$d_6$) d ppm 3.30 (s, 3H) 3.31-3.37 (m, 2H) 3.58-3.71 (m, 2H) 4.28 (s, 1H) 4.65 (s, 1H)

7.12-7.18 (m, 1H) 7.19-7.27 (m, 1H) 7.28-7.34 (m, 1H) 7.35-7.43 (m, 2H) 7.65 (d, J=6.80 Hz, 1H) 7.68-7.75 (m, 2H) 7.79 (t, J=6.42 Hz, 1H) 7.95 (d, J=7.55 Hz, 2H) 8.25-8.35 (m, 1H)

Example 56

Synthesis of N-(cyclohexylmethyl)-2-(2-(phenylsulfonyl)ethylthio)-nicotinamide 264 mg (1.62 mmol) of CDI were added to a solution of 500 mg (1.55 mmol) of 2-(2-(phenylsulfonyl)ethylthio)nicotinic acid in DCM (12 ml), and the mixture was stirred for 1 h at RT. A solution of 200 µl (1.55 mmol) of cyclohexanemethylamine in DCM (12 ml) was then added, and stirring was continued for a further 16 h at RT. The reaction solution was then washed in each case three times with sat. aq. ammonium chloride solution and saturated aqueous $NaHCO_3$ solution. The organic phase was dried over $MgSO_4$, filtered and concentrated in vacuo. 624 mg (1.49 mmol, 96%) of N-(cyclohexylmethyl)-2-(2-(phenylsulfonyl)ethylthio)nicotinamide were obtained as residue.
MS: m/z 419.1 [M+H]$^+$ Example 57

Synthesis of 2-(2-(phenylsulfonyl)ethylthio)-N-(1-(3-(trifluoromethyl)-phenyl)ethyl)nicotinamide 264 mg (1.62 mmol) of CDI were added to a solution of 500 mg (1.55 mmol) of 2-(2-(phenylsulfonyl)ethylthio)nicotinic acid in DCM (12 ml), and the mixture was stirred for 1 h at RT. A solution of 292 mg (1.55 mmol) of 1-(3-(trifluoromethyl)phenyl)ethylamine in DCM (12 ml) was then added, and stirring was continued for a further 16 h at RT. The reaction solution was then washed in each case three times with sat. aq. ammonium chloride solution and saturated aqueous NaCl solution. The organic phase was dried over $MgSO_4$, filtered and concentrated in vacuo. CC with the residue (ethyl acetate/hexane 1:1) yielded 462 mg (0.93 mmol, 60%) of 2-(2-(phenylsulfonyl)ethylthio)-N-(1-(3-(trifluoromethyl)phenyl)ethyl)nicotinamide. MS: m/z 495.1 [M+H]$^+$.

Example 58

Synthesis of N-(2-cyclohexylethyl)-2-(2-(phenylsulfonyl)ethylthio)-nicotinamide 158 mg (0.93 mmol) of CDI were added to a solution of 300 mg (0.93 mmol) of 2-(2-(phenylsulfonyl)ethylthio)nicotinic acid in DCM (8 ml), and the mixture was stirred for 1 h at RT. A solution of 151 mg (0.93 mmol) of 2-cyclohexylethylamine hydrochloride and 157 µL (0.93 mmol) of diisopropylethylamine in DCM (8 ml) was then added, and stirring was continued for a further 16 h at RT. The reaction solution was then washed in each case three times with sat. aq. ammonium chloride solution and saturated aqueous $NaHCO_3$ solution. The organic phase was dried over $MgSO_4$, filtered and concentrated in vacuo. 390 mg (0.90 mmol, 97%) of N-(2-cyclohexylethyl)-2-(2-(phenylsulfonyl)-ethyl-thio)nicotinamide were obtained as residue. MS: m/z 433.2 [M+H]$^+$.

Example 59

Synthesis of 2-(2-(cyclohexylthio)ethylthio)-N-(thiophen-2-ylmethyl)-nicotinamide 607 mg (4.4 mmol) of $K_2CO_3$ were added to a solution of 500 mg (2.0 mmol) of 2-mercapto-N-(thiophen-2-ylmethyl) nicotinamide (V1) in DMF (5 ml), and the mixture was stirred for 1 h at RT. 446 mg of (2-bromoethyl)-(cyclohexyl)sulfane (crude product V2) were then added, and stirring was continued for a further 18 h at RT. The mixture was then diluted with ethyl acetate, and water was added. The phases were separated and the aqueous phase was extracted with ethyl acetate. The combined organic phases were dried over $MgSO_4$, filtered and concentrated in vacuo. CC (ethyl acetate/n-hexane 1:1) with the residue yielded 268 mg (0.68 mmol, 34%) of 2-(2-(cyclohexylthio)ethylthio)-N-(thiophen-2-ylmethyl) nicotinamide. MS: m/z 393.1 [M+H]$^+$.

Example 100

Synthesis of 2-[2-(4-fluorophenyl)sulfonylethylthio]-N-(2-thienylmethyl)-nicotinamide 303 mg (2.2 mmol) of $K_2CO_3$ were added to a solution of 500 mg (2.0 mmol) of 2-mercapto-N-(thiophen-2-ylmethyl) nicotinamide in DMF (5 ml), and stirring was carried out for 30 min at RT. 445 mg (2.0 mmol) of 1-(2-chloroethylsulfonyl)-4-fluorobenzene were then added and stirring was continued for a further 2 days at RT. The mixture was then concentrated in vacuo, the residue was taken up in EA, and 1M aqueous $NaHCO_3$ solution was added. The phases were separated and the aqueous phase was extracted with EA. The combined organic phases were dried over $MgSO_4$, filtered through silica gel and concentrated in vacuo. CC (DCM/EA 4:1) of the residue yielded 365 mg (0.84 mmol, 48%) of 2-[2-(4-fluorophenyl)sulfonylethylthio]-N-(2-thienylmethyl)-nicotinamide. MS: m/z 437.0 [M+H]$^+$ Example 106

Synthesis of 2-[2-(3-fluorophenyl)sulfonylethylthio]-N-(2-thienylmethyl)-nicotinamide A solution of 408 mg (2.0 mmol) of 2-(3-fluorophenylsulfonyl)ethanol in DCM (5 ml) was cooled to 0° C.; 304 µl (2.2 mmol) of $NEt_3$ and 154 µl (2.0 mmol) of methanesulfonic acid chloride were added thereto, and stirring was carried out for 16 hours at RT. In another vessel, 275 mg (2.0 mmol) of $K_2CO_3$ were added to a solution of 500 mg (2.0 mmol) of 2-mercapto-N-(thiophen-2-ylmethyl)nicotinamide in DMF (6 ml), and stirring was carried out for 30 min at RT. The DCM reaction solution was added to this solution, and stirring was continued for 72 hours at RT. The mixture was then diluted with EA and washed with 1 N aqueous $NaHCO_3$ solution. The organic phase was dried over $MgSO_4$, filtered and concentrated in vacuo. CC (DCM/EA 4:1) of the residue yielded 194 mg (0.44 mmol, 22%) of 2-[2-(3-fluorophenyl)sulfonylethylthio]-N-(2-thienylmethyl)-nicotinamide. MS: m/z 437.0 [M+H]$^+$ Example 112

Synthesis of N-(2-thienylmethyl)-2-[2-[[2-(trifluoromethyl)phenyl]thio]-ethylthio]-nicotinamide 227 mg (1.65 mmol) of $K_2CO_3$ were added to a solution of 375 mg (1.5 mmol) of 2-mercapto-N-(thiophen-2-ylmethyl) nicotinamide in DMF (6 ml), and stirring was carried out for 60 min at RT. 361 mg (1.5 mmol) of (2-chloroethyl)(3-(trifluoromethyl)phenyl)sulfane were then added and stirring was continued for a further 16 h at RT. The mixture was then diluted with EA and extracted with water. The organic phase was dried over $MgSO_4$, filtered and concentrated in vacuo.

CC (hexane/EA 1:1) of the residue, followed by further CC (DCM/EA 19:1) of the resulting residue, yielded 274 mg (0.60 mmol, 40%) of N-(2-thienylmethyl)-2-[2-[[2-(trifluoromethyl)phenyl]thio]ethylthio]-nicotinamide. MS: m/z 455.0 [M+H]+

Example 141

Synthesis of 2-[2-(benzenesulfonyl)ethylthio]-6-methyl-N-(2-thienylmethyl)nicotinamide 336 mg (3.0 mmol) of potassium tert-butoxide were added at 0° C. to a solution of 607 mg (3.0 mmol) of 2-(phenylsulfonyl)ethanethiol in DMF (10 ml). After stirring for 10 min at 0° C., 534 mg (2.0 mmol) of 2-chloro-6-methyl-N-(thiophen-2-ylmethyl)nicotinamide were added and the mixture was then heated for 16 h at 50° C. Dilution with EA and washing with brine were then carried out. The organic phase was dried over Na$_2$SO$_4$, filtered and concentrated in vacuo. CC (hexane/EA 7:3) of the residue yielded 556 mg (1.28 mmol, 64%) of 2-[2-(benzenesulfonyl)ethylthio]-6-methyl-N-(2-thienylmethyl)-nicotinamide. MS: m/z 433.1 [M+H]+

Example 143

Synthesis of 2-[2-(benzenesulfonyl)ethylthio]-6-fluoro-N-(2-thienylmethyl)-nicotinamide 258 mg (2.3 mmol) of potassium tert-butoxide were added at 0° C. to a solution of 465 mg (2.3 mmol) of 2-(phenylsulfonyl)ethanethiol in DMF (7 ml). After stirring for 10 min at 0° C., 381 mg (1.5 mmol) of 2,6-difluoro-N-(thiophen-2-ylmethyl)nicotinamide were added and the mixture was then heated for 16 hours at 50° C. Dilution with EA and washing with brine were then carried out. The organic phase was dried over Na$_2$SO$_4$, filtered and concentrated in vacuo. CC (hexane/EA 7:3) of the residue yielded 298 mg (0.68 mmol, 45%) of 2-[2-(benzenesulfonyl)ethylthio]-6-fluoro-N-(2-thienylmethyl)-nicotinamide. MS: m/z 437.0 [M+H]+

Example 149

Synthesis of 2-[2-(benzenesulfonyl)ethylthio]-5-methyl-N-(2-thienylmethyl)nicotinamide 456 mg (1.2 mmol) of HATU and 680 µl (4.0 mmol) of DIPEA were added at 0° C. to a solution of 337 mg (1.0 mmol) of 5-methyl-2-(2-(phenylsulfonyl)ethylthio)nicotinic acid in DMF (3 ml). After stirring for a further 15 min at 0° C., 113 mg (1.0 mmol) of thiophen-2-ylmethylamine were added and stirring was carried out for 16 hours at RT. The mixture was then diluted with EA and washed in succession with sat. aq. citric acid solution, saturated aqueous Na$_2$CO$_3$ solution and brine. The organic phase was dried over Na$_2$SO$_4$, filtered and concentrated in vacuo. CC (hexane/EA 7:3) of the residue yielded 418 mg (0.97 mmol, 97%) of 2-[2-(benzenesulfonyl)ethylthio]-5-methyl-N-(2-thienylmethyl)-nicotinamide. MS: m/z 433.1 [M+H]+

Examples 60 to 88 and 94 to 150

The synthesis of Examples 60 to 88 and 94 to 150 was carried out according to the processes described for Examples 56 to 59, 100, 106, 112, 141, 143 and 149. Which examples were prepared by which process is summarized in Tables T4 and T5.

TABLE T4

| Example | Name | Synthesis analogous to example no. | Yield [%] | MS m/z [M + H]+ |
|---|---|---|---|---|
| 60 | N-(neopentyl)-2-(2-(phenylsulfonyl)ethylthio)nicotinamide | 56 | 71 | 393.1 |
| 61 | N-(5-methylfuran-2-ylmethyl)-2-(2-(phenylsulfonyl)ethylthio)nicotinamide | 56 | 83 | 417.1 |
| 62 | N-(furan-2-ylmethyl)-2-(2-(phenylsulfonyl)ethylthio)nicotinamide | 56 | 75 | 403.1 |
| 63 | 2-(2-(phenylsulfonyl)ethylthio)-N-(tetrahydro-2H-pyran-4-ylmethyl)-nicotinamide | 56 | 90 | 421.1 |
| 64 | 2-(2-(phenylsulfonyl)ethylthio)-N-(4-(trifluoromethylthio)benzyl)-nicotinamide | 57 | 50 | 513.1 |
| 65 | 2-(2-(phenylsulfonyl)ethylthio)-N-(3-tolylmethyl)nicotinamide | 57 | 28 | 427.1 |
| 66 | (R)—N-(1-cyclohexylethyl)-2-(2-(phenylsulfonyl)ethylthio)nicotinamide | 57 | 31 | 433.2 |
| 67 | N-(1-(3,4-dimethylphenyl)ethyl)-2-(2-(phenylsulfonyl)ethylthio)nicotinamide | 57 | 54 | 455.1 |
| 68 | N-(1-thiophen-2-ylethyl)-2-(2-(phenylsulfonyl)ethylthio)nicotinamide | 57 | 57 | 433.1 |
| 69 | N-(1-(3,5-dimethylphenyl)methyl)-2-(2-(phenylsulfonyl)ethylthio)-nicotinamide | 57 | 52 | 441.1 |
| 70 | N-(cyclohexylmethyl)-2-(2-(3-trifluoromethylphenylsulfonyl)ethylthio)-nicotinamide | 57 | 40 | 487.1 |
| 71 | (S)—N-(1-cyclohexylethyl)-2-(2-(phenylsulfonyl)ethylthio)nicotinamide | 57 | 44 | 433.2 |
| 72 | N-(1-(3,5-dimethylphenyl)ethyl)-2-(2-(phenylsulfonyl)ethylthio)nicotinamide | 57 | 46 | 455.1 |
| 73 | N-(thiophen-2-ylmethyl)-2-(2-(3-(trifluoromethyl)phenylthio)ethylthio)-nicotinamide | 59 | 25 | 455.0 |

TABLE T4-continued

| Example | Name | Synthesis analogous to example no. | Yield [%] | MS m/z [M + H]$^+$ |
|---|---|---|---|---|
| 74 | N-(cyclopentylmethyl)-2-(2-(3-trifluoromethylphenylsulfonyl)ethylthio)nicotinamide | 57 | 73 | 405.1 |
| 75 | N-(cyclobutylmethyl)-2-(2-(3-trifluoromethylphenylsulfonyl)ethylthio)nicotinamide | 58 | 62 | 391.1 |
| 76 | N-((1,4-dioxan-2-yl)methyl)-2-(2-(phenylsulfonyl)ethylthio)nicotinamide | 57 | 57 | 423.1 |
| 77 | 2-(2-(phenylsulfonyl)ethylthio)-N-(4-(pyridin-2-yloxy)benzyl)nicotinamide | 58 | 52 | 506.1 |
| 78 | N-(2-methylbutyl)-2-(2-(phenylsulfonyl)ethylthio)nicotinamide | 56 | 59 | 393.1 |
| 79 | N-(2-ethylbutyl)-2-(2-(phenylsulfonyl)ethylthio)nicotinamide | 56 | 60 | 407.1 |
| 80 | N-(cyclopropylmethyl)-2-(2-(3-trifluoromethylphenylsulfonyl)ethylthio)nicotinamide | 56 | 61 | 377.1 |
| 81 | N-(3-(2-methoxyethoxy)propyl)-2-(2-(phenylsulfonyl)ethylthio)nicotinamide | 56 | 58 | 439.1 |
| 82 | 2-(2-(phenylsulfonyl)ethylthio)-N-(1-(4-(trifluoromethylthio)phenyl)ethyl)nicotinamide | 56 | 38 | 527.1 |
| 83 | N-(3-(1H-pyrazol-1-yl)benzyl)-2-(2-(phenylsulfonyl)ethylthio)nicotinamide | 57 | 57 | 479.1 |
| 84 | N-((2,3-dihydrobenzofuran-5-yl)methyl)-2-(2-(phenylsulfonyl)ethylthio)nicotinamide | 58 | 57 | 455.1 |
| 85 | N-(4-phenoxybenzyl)-2-(2-(phenylsulfonyl)ethylthio)nicotinamide | 57 | 52 | 505.1 |
| 86 | N-(((1R,2S,5R)-6,6-dimethylbicyclo-[3.1.1]heptan-2-yl)methyl)-2-(2-(phenylsulfonyl)ethylthio)nicotinamide | 57 | 75 | 459.2 |
| 87 | N-(thiophen-2-ylmethyl)-2-(2-(3-(trifluoromethyl)phenylsulfonyl)ethylthio)nicotinamide | 57 | 64 | 487.0* |
| 88 | 2-(2-(phenylsulfonyl)ethylthio)-N-(3-(trifluoromethyl)benzyl)nicotinamide | 57 | 71 | 481.1 |

Further tested compounds:

89 2-(2-(phenylsulfonyl)ethylthio)-N-(thiophen-2-ylmethyl)nicotinamide
90 N-(pyridin-2-ylmethyl)-2-(2-(3-trifluoromethyl)phenylsulfonyl)-ethylthio)nicotinamide
91 N-(pyridin-2-ylmethyl)-2-(2-(5-(trifluoromethyl)pyridin-2-ylsulfonyl)-ethylthio)nicotinamide
92 N-(thiophen-2-ylmethyl)-2-(2-(5-(trifluoroethyl)pyridin-2-ylsulfonyl)-ethylthio)nicotinamide Example 93

Synthesis of N-(isobutyl)-2-(2-(phenylsulfonyl)ethylthio)nicotinamide 171 mg (1.05 mmol) of CDI were added to a solution of 323 mg (1.00 mmol) of 2-(2-(phenylsulfonyl)ethylthio)nicotinic acid in DCM (16 ml), and the mixture was stirred for 1 hour at RT. 99 µl (1.00 mmol) of isobutylamine were then added, and stirring was continued for a further 5 days at RT. The reaction solution was then washed in each case twice with a 4 M aq. ammonium chloride solution and a 1 M aq. sodium hydrogen carbonate solution. The organic phase was dried over MgSO$_4$, filtered and concentrated in vacuo. The residue obtained was taken up in ethyl acetate (30 ml) and washed with 0.4 M hydrochloric acid (5 ml). The organic phase was again dried over MgSO$_4$, filtered and concentrated in vacuo. 160 mg (0.42 mmol, 42 of N-(isobutyl)-2-(2-(phenylsulfonyl)ethylthio)nicotinamide were obtained as residue. MS: m/z 379.1 [M+H]$^+$

TABLE T5

| Example | Name | Synthesis analogous to example no. | Yield [%] | MS m/z [M + H]$^+$ |
|---|---|---|---|---|
| 94 | 2-[2-(benzenesulfonyl)ethylthio]-N-(2-tetrahydropyranylmethyl)-nicotinamide | 57 | 53 | 421.1 |

TABLE T5-continued

| Example | Name | Synthesis analogous to example no. | Yield [%] | MS m/z [M + H]+ |
|---|---|---|---|---|
| 95 | 2-[2-(benzenesulfonyl)ethylthio]-N-[(5-methyl-2-thienyl)methyl]-nicotinamide | 57 | 80 | 433.1 |
| 96 | 2-[2-(benzenesulfonyl)ethylthio]-N-[(4-methyl-2-thienyl)methyl]-nicotinamide | 57 | 84 | 433.1 |
| 97 | N-(1-adamantylmethyl)-2-[2-(benzenesulfonyl)ethylthio]-nicotinamide | 57 | 39 | 471.2 |
| 98 | 2-[2-(benzenesulfonyl)ethylthio]-N-[(3-morpholinophenyl)methyl]-nicotinamide | 57 | 67 | 498.1 |
| 99 | 2-[2-(4-chlorophenyl)sulfonylethylthio]-N-(2-thienylmethyl)-nicotinamide | 100 | 27 | 453.0 |
| 101 | N-(2-thienylmethyl)-2-[2-[3-(trifluoromethoxy)phenyl]sulfonylethylthio]-nicotinamide | 100 | 42 | 503.0 |
| 102 | N-(2-thienylmethyl)-2-[2-[4-(trifluoromethyl)phenyl]sulfonylethylthio]-nicotinamide | 100 | 76 | 487.0 |
| 103 | N-(2-thienylmethyl)-2-[2-[4-(trifluoromethoxy)phenyl]sulfonylethylthio]-nicotinamide | 100 | 24 | 503.0 |
| 104 | 2-[2-(m-tolylsulfonyl)ethylthio]-N-(2-thienylmethyl)-nicotinamide | 100 | 19 | 433.1 |
| 105 | 2-[2-(m-tolylthio)ethylthio]-N-(2-thienylmethyl)-nicotinamide | 112 | 38 | 401.1 |
| 107 | 2-[2-(benzenesulfonyl)ethylthio]-N-(3,3-dimethylbutyl)-nicotinamide | 57 | 80 | 407.1 |
| 108 | 2-[2-(benzenesulfonyl)ethylthio]-N-(2-benzothiophenylmethyl)-nicotinamide | 57 | 60 | 469.1 |
| 109 | 2-[2-(phenylthio)ethylthio]-N-(2-thienylmethyl)-nicotinamide | 112 | 26 | 387.1 |
| 110 | 2-[2-(benzenesulfinyl)ethylthio]-N-(2-thienylmethyl)-nicotinamide | 112 | 26 | 403.1 |
| 111 | 2-(2-cyclohexylsulfonylethylthio)-N-(2-thienylmethyl)-nicotinamide | 112 | 11 | 425.1 |
| 113 | N-(2-thienylmethyl)-2-[2-[2-(trifluoromethyl)phenyl]sulfinylethylthio]-nicotinamide | 112 | 41 | 471.0 |
| 114 | N-(2-thienylmethyl)-2-[2-[2-(trifluoromethyl)phenyl]sulfonylethylthio]-nicotinamide | 100 | 39 | 487.0 |
| 115 | 2-[2-(benzenesulfonyl)ethylthio]-N-[(5-chloro-2-thienyl)methyl]-nicotinamide | 57 | 61 | 453.0 |
| 116 | 2-[2-(2-fluorophenyl)sulfonylethylthio]-N-(2-thienylmethyl)-nicotinamide | 100 | 17 | 437.0 |
| 117 | 2-[2-[3,5-bis(trifluoromethyl)phenyl]sulfonylethylthio]-N-(2-thienylmethyl)-nicotinamide | 100 | 12 | 555.0 |
| 118 | 2-[2-(3-methoxyphenyl)sulfonylethylthio]-N-(2-thienylmethyl)-nicotinamide | 100 | 28 | 449.1 |
| 119 | 2-[2-(4-methoxyphenyl)sulfonylethylthio]-N-(2-thienylmethyl)-nicotinamide | 100 | 33 | 449.1 |
| 120 | 2-[2-(benzenesulfonyl)ethylthio]-N-(4-tetrahydrothiopyranylmethyl)-nicotinamide | 57 | 60 | 437.1 |
| 121 | 2-[2-(4-ethylphenyl)sulfonylethylthio]-N-(2-thienylmethyl)-nicotinamide | 57 | 16 | 447.1 |
| 122 | N-(2-thienylmethyl)-2-[2-[[4-(trifluoromethyl)phenyl]thio]ethylthio]-nicotinamide | 112 | 41 | 455.0 |
| 123 | 2-[2-(o-tolylthio)ethylthio]-N-(2-thienylmethyl)-nicotinamide | 112 | 25 | 401.1 |
| 124 | 2-[2-[(3-fluorophenyl)thio]ethylthio]-N-(2-thienylmethyl)-nicotinamide | 112 | 39 | 405.0 |
| 125 | 2-[2-[(3,4-difluorophenyl)thio]ethylthio]-N-(2-thienylmethyl)-nicotinamide | 112 | 42 | 423.0 |
| 126 | 2-[2-[(2,4-difluorophenyl)thio]ethylthio]-N-(2-thienylmethyl)-nicotinamide | 112 | 41 | 423.0 |
| 127 | 2-[2-(benzenesulfonyl)ethylthio]-N-[2-(2-thienyl)ethyl]-nicotinamide | 57 | 60 | 433.1 |
| 128 | 2-[2-(benzenesulfonyl)ethylthio]-N-phenthyl-nicotinamide | 57 | 63 | 427.1 |
| 129 | 2-[2-(benzenesulfonyl)ethylthio]-N-(3-phenylpropyl)-nicotinamide | 57 | 60 | 441.1 |
| 130 | 2-[2-(3,4-difluorophenyl)sulfonylethylthio]-N-(2-thienylmethyl)-nicotinamide | 100 | 50 | 455.0 |
| 131 | 2-[2-(2,4-difluorophenyl)sulfonylethylthio]-N-(2-thienylmethyl)-nicotinamide | 100 | 67 | 455.0 |

TABLE T5-continued

| Example | Name | Synthesis analogous to example no. | Yield [%] | MS m/z [M + H]+ |
|---|---|---|---|---|
| 132 | 2-[2-[(2-fluorophenyl)thio]ethylthio]-N-(2-thienylmethyl)-nicotinamide | 112 | 40 | 405.0 |
| 133 | 2-[2-[(4-fluorophenyl)thio]ethylthio]-N-(2-thienylmethyl)-nicotinamide | 112 | 43 | 405.0 |
| 134 | 2-[2-[(4-chlorophenyl)thio]ethylthio]-N-(2-thienylmethyl)-nicotinamide | 112 | 49 | 421.0 |
| 135 | 2-[2-(p-tolylthio)ethylthio]-N-(2-thienyl-methyl)-nicotinamide | 112 | 52 | 401.1 |
| 136 | 2-[2-(benzenesulfonyl)ethylthio]-N-isopentyl-nicotinamide | 57 | 53 | 393.1 |
| 137 | 2-[2-(benzenesulfonyl)ethylthio]-N-(2-cyclopropylethyl)-nicotinamide | 57 | 57 | 391.1 |
| 138 | 2-[2-(benzenesulfonyl)ethylthio]-N-(2-cyclopentylethyl)-nicotinamide | 57 | 40 | 419.1 |
| 139 | N-(3,3-dimethylbutyl)-2-[2-[3-(trifluoro-methyl)phenyl]sulfonylethylthio]-nicotinamide | 57 | 17 | 475.1 |
| 140 | N-(cyclopentylmethyl)-2-[2-[3-(trifluoro-methyl)phenyl]sulfonylethylthio]-nicotinamide | 57 | 26 | 473.1 |
| 142 | 2-[2-(benzenesulfonyl)ethylthio]-N-(2-thienylmethyl)-6-(trifluoromethyl)-nicotinamide | 141 | 41 | 487.0 |
| 144 | 2-[2-(benzenesulfonyl)ethylthio]-N-[(3-methylcyclohexyl)methyl]-nicotinamide | 57 | | 433.2 |
| 145 | 2-[2-(benzenesulfonyl)ethylthio]-N-(cycloheptylmethyl)-nicotinamide | 57 | | 433.2 |
| 146 | 2-[2-(benzenesulfonyl)ethylthio]-N-[(2-methylcyclohexyl)methyl]-nicotinamide | 57 | | 433.2 |
| 147 | 2-[2-(benzenesulfonyl)ethylthio]-N-[(4-methylcyclohexyl)methyl]-nicotinamide | 57 | | 433.2 |
| 148 | 2-[2-(benzenesulfonyl)ethylthio]-5-fluoro-N-(2-thienylmethyl)-nicotinamide | 143 | | 437.0 |
| 150 | 2-[2-(benzenesulfonyl)ethylthio]-N-(2-thienylmethyl)-5-(trifluoromethyl)-nicotinamide | 141 | | 487.0 |

Biological Data
Fluorescence Assay Using a Voltage Sensitive Dye

Human CHO-K1 cells expressing KCNQ2/3 channels are cultivated adherently at 37° C., 5% $CO_2$ and 95% humidity in cell culture bottles (e.g. 80 $cm^2$ TC flasks, Nunc) with DMEM-high glucose (Sigma Aldrich, D7777) including 10% FCS (PAN Biotech, e.g. 3302-P270521) or alternatively with MEM Alpha Medium (1×, liquid, Invitrogen, #22571), 10% fetal calf serum (FCS) (Invitrogen, #10270-106, heat-inactivated) and the necessary selection antibiotics.

Before being distributed for the measurements, the cells are washed with a 1×DPBS buffer without $Ca^{2+}/Mg^{2+}$ (e.g. Invitrogen, #14190-094) and detached from the bottom of the culture vessel by means of Accutase (PAA Laboratories, #L11-007) (incubation with Accutase for 15 min at 37° C.). The cell count then present is determined using a CASY™ cell counter (TCC model, Schärfe System) in order subsequently to apply, according to density optimization for the individual cell line, 20,000-30,000 cells/well/100 µl of the described nutrient medium to 96-well measuring plates of the Corning™ CellBIND™ type (Flat Clear Bottom Black Polystyrene Microplates, #3340). Incubation is then carried out for one hour at room temperature, without gassing or adjusting the humidity, followed by incubation for 24 hours at 37° C., 5% $CO_2$ and 95% humidity.

The voltage-sensitive fluorescent dye from the Membrane Potential Assay Kit (Red™ Bulk format part R8123 for FLIPR, MDS Analytical Technologies™) is prepared by dissolving the contents of a vessel Membrane Potential Assay Kit Red Component A in 200 ml of extracellular buffer (ES buffer, 120 mM NaCl, 1 mM KCl, 10 mM HEPES, 2 mM $CaCl_2$, 2 mM $MgCl_2$, 10 mM glucose; pH 7.4). After removal of the nutrient medium, the cells are washed with 200 µl of ES buffer, then covered with a layer of 100 µl of the dye solution prepared above and incubated for 45 min at room temperature with the exclusion of light.

The fluorescence measurements are carried out with a BMG Labtech FLUOstar™ or BMG Labtech NOVOstar™ or BMG Labtech POLARstar™ instrument (525 nm excitation, 560 nm emission, Bottom Read mode). After incubation of the dye, 50 µl of the test substances in the desired concentrations, or 50 µl of ES buffer for control purposes, are introduced into separate cavities of the measuring plate and incubated for 30 min at room temperature while being shielded from light. The fluorescence intensity of the dye is then measured for 5 min and the fluorescence value $F_1$ of each well is thus determined at a given, constant time. 15 µL of a 100 mM KCl solution (final concentration 92 mM) are then added to each well. The change in fluorescence is subsequently measured until all the relevant measured values have been obtained (mainly 5-30 min). At a given time after KCl application, a fluorescence value $F_2$ is determined, in this case at the time of the fluorescence peak.

For calculation, the fluorescence intensity $F_2$ is compared with the fluorescence intensity $F_1$, and the agonistic activity of the target compound on the potassium channel is determined therefrom. $F_2$ and $F_1$ are calculated as follows:

$$\left(\frac{F_2 - F_1}{F_1}\right) \times 100 = \frac{\Delta F}{F}(\%)$$

In order to determine whether a substance has an agonistic activity, $$\frac{\Delta F}{F},$$

for example, can be compared with $$\left(\frac{\Delta F}{F}\right)_K$$

of control cells.

$$\left(\frac{\Delta F}{F}\right)_K$$

is determined by adding to the reaction batch only the buffer solution instead of the substance to be tested, determining the value $F_{1K}$ of the fluorescence intensity, adding the potassium ions as described above and measuring a value $F_{2K}$ of the fluorescence intensity. Then $F_{2K}$ and $F_{1K}$ are calculated as follows:

$$\left(\frac{F_{2K} - F_{1K}}{F_{1K}}\right) \times 100 = \left(\frac{\Delta F}{F}\right)_K(\%)$$

A substance has an agonistic activity on the potassium channel when $$\frac{\Delta F}{F}$$

is greater than $$\left(\frac{\Delta F}{F}\right)_K:$$

$$\frac{\Delta F}{F} > \left(\frac{\Delta F}{F}\right)_K$$

Independently of the comparison of $$\frac{\Delta F}{F} \text{ with } \left(\frac{\Delta F}{F}\right)_K,$$

it is also possible to conclude that a target compound has agonistic activity if an increase in $$\frac{\Delta F}{F}$$

is to be observed as the dosage of the target compound increases.

Calculations of $EC_{50}$ and $IC_{50}$ values are carried out with the aid of "Prism v4.0" software (GraphPad Software™). The following values were determined by way of example:

TABLE T6

| Example | % inhibition [10 μM] or $EC_{50}$ |
|---|---|
| 1 | 14.2 |
| 2 | — |
| 3 | 20.8 |
| 4 | — |
| 5 | 1.86 ($EC_{50}$) |
| 6 | — |
| 7 | — |
| 8 | 1.28 ($EC_{50}$) |
| 9 | — |
| 10 | — |
| 11 | 1.17 ($EC_{50}$) |
| 12 | 1.8 ($EC_{50}$) |
| 13 | 1.4 ($EC_{50}$) |
| 14 | 19.1 |
| 15 | 2.48 ($EC_{50}$) |
| 16 | — |
| 17 | 6.52 ($EC_{50}$) |
| 18 | 15.3 |
| 19 | 1.27 ($EC_{50}$) |
| 20 | 1.28 ($EC_{50}$) |
| 21 | 7.9 |
| 22 | 24.7 |
| 23 | — |
| 24 | 19.1 |
| 25 | 1.28 ($EC_{50}$) |
| 26 | — |
| 29 | 90 |
| 33 | — |
| 34 | 9.4 |
| 35 | — |
| 36 | 4.11 ($EC_{50}$) |
| 37 | 15.5 |
| 38 | 1.4 |
| 39 | 6.09 ($EC_{50}$) |
| 40 | 7.9 |
| 41 | 2.39 ($EC_{50}$) |
| 42 | — |
| 43 | 1.97 ($EC_{50}$) |
| 44 | 2.23 ($E0_{50}$) |
| 45 | 2.14 ($EC_{50}$) |
| 46 | 7.4 |
| 47 | 17.5 |
| 48 | 7.7 |
| 49 | 7.6 ($EC_{50}$) |
| 50 | 6 |
| 51 | 4.12 ($EC_{50}$) |
| 52 | 1.82 ($EC_{50}$) |
| 54 | 2.34 ($EC_{50}$) |
| 55 | 16.52 ($EC_{50}$) |
| 56 | 1.01 ($EC_{50}$) |
| 57 | 5.7 ($EC_{50}$) |
| 58 | 1.18 ($EC_{50}$) |
| 59 | 91 |
| 60 | 9.59 ($EC_{50}$) |
| 61 | 3.47 ($EC_{50}$) |
| 62 | 4.39 ($EC_{50}$) |
| 64 | 0.88 ($EC_{50}$) |
| 65 | 0.58 ($EC_{50}$) |
| 66 | 40 |
| 67 | 32 |

TABLE T6-continued

| Example | % inhibition [10 μM] or $EC_{50}$ |
|---|---|
| 70 | 106 |
| 71 | 20 |
| 72 | 45 |
| 73 | 107 |
| 74 | 130 |
| 75 | 64 |
| 76 | 52 |
| 77 | 83 |
| 78 | 112 |
| 79 | 76 |
| 80 | 38 |
| 83 | 32 |
| 84 | 81 |
| 85 | 88 |
| 86 | 88 |
| 87 | 103 |
| 89 | 2.28 ($EC_{50}$) |
| 90 | 2.49 ($EC_{50}$) |
| 92 | 2.74 ($EC_{50}$) |
| 99 | 0.234 ($EC_{50}$) |
| 100 | 0.503 ($EC_{50}$) |
| 101 | 156 |
| 102 | 0.197 ($EC_{50}$) |
| 103 | 83 |
| 104 | 151 |
| 105 | 0.168 ($EC_{50}$) |
| 106 | 0.187 ($EC_{50}$) |
| 107 | 1.418 ($EC_{50}$) |
| 108 | 57 |
| 109 | 0.075 ($EC_{50}$) |
| 110 | 64 |
| 111 | 63 |
| 112 | 141 |
| 113 | 52 |
| 114 | 77 |
| 115 | 131 |
| 116 | 107 |
| 117 | 93 |
| 118 | 145 |
| 119 | 57 |
| 120 | 72 |
| 121 | 73 |
| 122 | 108 |
| 123 | 137 |
| 124 | 151 |
| 125 | 147 |
| 126 | 150 |
| 127 | 75 |
| 128 | 48 |
| 129 | 132 |
| 130 | 147 |
| 131 | 116 |
| 132 | 133 |
| 133 | 142 |
| 134 | 150 |
| 135 | 125 |
| 141 | 115 |
| 142 | 62 |
| 143 | 114 |
| 144 | 147 |
| 145 | 164 |
| 146 | 101 |
| 147 | 131 |
| 148 | 117 |
| 149 | 46 |

Voltage Clamp Measurements

In order to confirm a KCNQ2/3-agonistic action of the substances electrophysiologically, patch-clamp measurements (Hamill et al., 1981) were carried out in voltage clamp mode on a stably transfected hKCNQ2/3 CHO-K1 cell line. After formation of the gigaseal, the cells were first clamped at a holding potential of −60 mV. Thereafter, depolarizing voltage jumps were applied up to a potential of +20 mV (increment: 20 mV, duration: 1 second) in order to confirm the functional expression of KCNQ2/3-typical currents. The testing of the substances was carried out at a potential of −40 mV. The increase in current induced by retigabine (10 μM) at −40 mV was first recorded as a positive control on each cell. After complete washing out of the retigabine effect (duration: 80 s), the test substance (10 μM) was applied. The increase in current induced by the test substance was standardized to the retigabine effect and indicated as the relative efficacy (see below). Hamill O P, Marty A, Neher E, Sakmann B, Sigworth F J.: Improved patch-clamp techniques for high-resolution current recording from cells and cell-free membrane patches. *Pflugers Arch.* 1981 August; 391(2):85-100. Voltage-clamp measurements were carried out only for selected compounds:

TABLE T7

| Example | MAN rel eff @ 10 μm [RG = 1] | MAN $EC_{50}$ [μM] |
|---|---|---|
| 56 | 1.06 | |
| 58 | 0.47 | |
| 61 | 0.81 | |
| 65 | 0.4 | |
| 89 | | 1.01 |
| 90 | 0.79 | |

Formalin Test, Rat

The investigations to determine the antinociceptive activity of the compounds were carried out in the formalin test on male rats (Sprague-Dawley, 150-170 g).

In the formalin test, a distinction is made between the first (early) phase (0-15 min after formalin injection) and the second (late) phase (15-60 min after formalin injection) (D. Dubuisson, S. G. Dennis, Pain 4, 161-174 (1977)). The early phase, as a direct reaction to the formalin injection, represents a model for acute pain, while the late phase is regarded as a model for persistent (chronic) pain (T. J. Coderre, J. Katz, A. L. Vaccarino, R. Meizack, Pain, Vol. 52, p. 259, 1993).

The compounds according to the invention were investigated in the second phase of the formalin test in order to obtain information about the activity of substances in the case of chronic/inflammatory pain.

A nociceptive reaction was induced in freely mobile test animals by means of a single subcutaneous formalin injection (50 μl, 5% strength) into the dorsal side of the right rear paw, the reaction manifesting itself in the following behaviour parameters: lifting and holding of the affected paw (score 1), shaking or twitching (score 2), licking and biting (score 3). The differing behaviors induced by the formalin injection were detected continuously by observation of the animals in the late phase of the formalin test and were weighted differently in an evaluation. Normal behavior, in which the animal puts its weight on all four paws equally, was recorded as score 0. The time of administration before the formalin injection was chosen in dependence on the mode of administration of the compounds according to the invention (intraperitoneal: 15 min, intravenous: 5 min). After injection of substances that have antinociceptive activity in the formalin test, the described behaviours (score 1-3) of the animals are reduced or even eliminated. Comparison was made with control animals which had received the vehicle (solvent) prior to formalin administration. The nociceptive behaviour was calculated as the so-called pain rate (PR). The various behaviour parameters were given a different weighting (factor 0, 1, 2, 3). Calculation was carried out at 3-minute intervals according to the following formula:

$$PR = [(T_0 \times 0) + (T_1 \times 1) + (T_2 \times 2) + (T_3 \times 3)]/180$$

where $T_0$, $T_1$, $T_2$ and $T_3$ each correspond to the time in seconds at which the animal exhibited the behavior 0, 1, 2 or 3. Substance and vehicle groups each contain n=10 animals. Based on the PR calculations, the activity of the substance was determined as the change compared with the control in percent.

TABLE T8

| Example | Mode of administration | Change in % |
|---------|------------------------|-------------|
| 56 | 2.15 mg/kg i.v. | −34.1 |
| 73 | 1 mg/kg i.v. | −29.9 |
| 89 | 6.81 mg/kg i.v. | −74.2 |

In addition, Example 89 was investigated in the Chung test on the rat. In the case of i.v. administration, a $ED_{50}$ of 6.3 mg/kg was determined (Kim, S. H. and Chung, J. M., An experimental model for peripheral neuropathy produced by segmental spinal nerve ligation in the rat, Pain, 50 (1992) 355-363).

| | Abbreviations |
|---|---|
| aq. | Aqueous |
| Brine | saturated aqueous NaCl solution |
| CDI | 1,1'-carbonyldiimidazole |
| D | Days |
| DCC | N,N'-dicyclohexylcarbodiimide |
| DCM | Dichloromethane |
| DIPEA | Diisopropylethylamine |
| DMAP | 4-(dimethylamino)-pyridine |
| DMF | N,N-dimethylformamide |
| DMSO | dimethyl sulfoxide |
| EDCI | N-(3-dimethylaminopropyl)-N'-ethyl-carbodiimide |
| EA | ethyl acetate |
| sat. | Saturated |
| H | hour(s) |
| HATU | O-(7-aza-benzotriazol-1-yl)-N,N,N',N'-tetramethyluronium hexafluorophosphate |
| HBTU | O-(benzotriazol-1-y1)-N,N,N',N'-tetramethyluronium hexafluorophosphate |
| HMPT | hexamethylphosphoric acid triamide |
| HOBt | 1-hydroxy-1H-benzotriazole |
| M | Molar |
| m/z | mass/charge ratio |
| MeOH | Methanol |
| Min | Minutes |
| MS | mass spectrometry |
| RT | room temperature 23 ± 7° C. |
| CC | column chromatography on silica gel |
| THF | Tetrahydrofuran |
| Vv | volume ratio |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

The invention claimed is:

1. A substituted nicotinamide compound corresponding to formula I

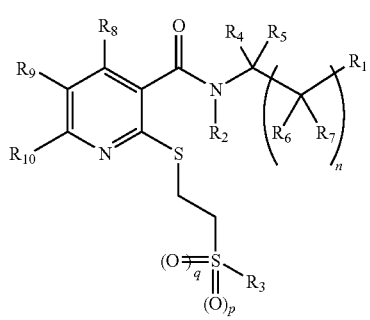

wherein n=0, 1 or 2;

p=0 or 1;

q=0 or 1;

$R^1$ denotes aryl or heteroaryl, each unsubstituted or mono- or poly-substituted; $C_{1-6}$-alkyl, $C_{3-10}$-cycloalkyl or heterocyclyl, each unsubstituted or mono- or poly-substituted;

$R^2$ denotes H or $C_{1-6}$-alkyl, unsubstituted or mono- or poly-substituted;

$R^3$ denotes aryl or heteroaryl, unsubstituted or mono- or poly-substituted; $C_{1-6}$-alkyl or $C_{3-10}$-cycloalkyl, in each case unsubstituted or mono- or poly-substituted;

$R^4$, $R^5$, $R^6$ and $R^7$ each independently denote H or $C_{1-6}$-alkyl, unsubstituted or mono- or poly-substituted; and $R^8$, $R^9$ and $R^{10}$ each independently denote H, F, Cl, Br, O—$C_{1-6}$-alkyl, $CF_3$, $OCF_3$, $SCF_3$, or $C_{1-6}$-alkyl;

with the proviso that when $R^3$ is 3-trifluoromethylphenyl or 4-trifluoromethyl-2-pyridyl, $R^2$, $R^4$ and $R^5$ each denote H, and n is 0, then $R^1$ is not 2-pyridyl or 2-thienyl; and when $R^3$ is phenyl or methyl, $R^2$, $R^4$ and $R^5$ each denote H, and n is 0, then $R^1$ is not 2-thienyl;

wherein the substituents on the alkyl, heterocyclyl or cycloalkyl groups replace one or more hydrogen atoms with one or more identical or different substituents selected from the group consisting of F, Cl, Br, I, —CN, $NH_2$, NH—$C_{1-6}$-alkyl, NH—$C_{1-6}$-alkyl-OH, N($C_{1-6}$-alkyl)$_2$, N($C_{1-6}$-alkyl-OH)$_2$, $NO_2$, SH, S—$C_{1-6}$-alkyl, S-benzyl, O—$C_{1-6}$-alkyl, OH, O—$C_{1-6}$-alkyl-OH, =O, O-benzyl, C(=O)$C_{1-6}$-alkyl, $CO_2H$, $CO_2$—$C_{1-6}$-alkyl, phenyl, phenoxy, morpholinyl, piperidinyl, pyrrolidinyl and benzyl; and the substituents on the aryl or heteroaryl groups replace one or more hydrogen atoms with one or more identical or different substituents selected from the group consisting of F, Cl, Br, I, CN, $NH_2$, NH—$C_{1-6}$-alkyl, NH—$C_{1-6}$-alkyl-OH, N($C_{1-6}$-alkyl)$_2$, N($C_{1-6}$-alkyl-OH)$_2$, $NO_2$, SH, S—$C_{1-6}$-alkyl, OH, O—$C_{1-6}$-alkyl, O—$C_{1-6}$alkyl-OH, C(=O)$C_{1-6}$-alkyl, C(=O)NH$C_{1-6}$-alkyl; o-pyridyl; C(=O)-aryl; C(=O)—N-morpholine; C(=O)-piperidine; (C=O)-pyrrolidine; (C=O)-piperazine; NHSO$_2$$C_{1-6}$-alkyl, NHCO$C_{1-6}$-alkyl, $CO_2H$, $CH_2SO_2$-phenyl, $CO_2$—$C_{1-6}$-alkyl, $OCF_3$, $SCF_3$, $CF_3$,

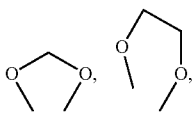

C$_{1-6}$-alkyl, pyrrolidinyl, piperidinyl, morpholinyl, benzyloxy, phenoxy, phenyl, pyridyl, alkylaryl, imidazolyl, pyrazolyl, thienyl and furyl;

or a salt thereof with a physiologically acceptable acid.

2. A compound as claimed in claim 1, wherein said compound is present in the form of an isolated stereoisomer.

3. A compound as claimed in claim 1, wherein said compound is present in the form of a mixture of stereoisomers in any mixing ratio.

4. A compound as claimed in claim 3, wherein said compound is present in the form of a racemic mixture.

5. A substituted nicotinamide compound as claimed in claim 1, wherein p and q each denote 1.

6. A substituted nicotinamide compound as claimed in claim 1, wherein R$^1$ denotes tert-butyl, phenyl, pyridyl, thienyl, furyl or cyclohexyl, each unsubstituted or mono- or poly-substituted.

7. A substituted nicotinamide compound as claimed in claim 6, wherein R$^1$ denotes
cyclohexyl, unsubstituted or mono- or poly-substituted by F, CH$_3$, Cl, Br, or OCH$_3$;
phenyl, unsubstituted or mono- or poly-substituted by F, CH$_3$, Cl, Br, CF$_3$, OCH$_3$, SCF$_3$ or OCF$_3$; or
pyridyl, thienyl or furyl, each unsubstituted or mono- or poly-substituted by CH$_3$.

8. A substituted nicotinamide compound as claimed in claim 1, wherein R$^2$ denotes CH$_3$ or H.

9. A substituted nicotinamide compound as claimed in claim 1, wherein R$^4$, R$^5$, R$^6$ and R$^7$ each independently denote H or CH$_3$.

10. A substituted nicotinamide compound as claimed in claim 1, wherein n denotes 0 or 1.

11. A substituted nicotinamide compound as claimed in claim 1, wherein R$^3$ denotes aryl or heteroaryl, each unsubstituted or mono- or poly-substituted.

12. A substituted nicotinamide compound as claimed in claim 11, wherein R$^3$ denotes phenyl which is unsubstituted or substituted by CF$_3$ or CH$_3$.

13. A substituted nicotinamide compound selected from the group consisting of:
1   2-(2-(phenylsulfonyl)ethylthio)-N-(pyridine-2-ylmethyl)nicotinamide
2   2-(2-(phenylsulfonyl)ethylthio)-N-(pyridine-4-ylmethyl)nicotinamide
3   N-(3-fluorophenethyl)-2-(2-(phenylsulfonyl)ethylthio)nicotinamide
4   N-methyl-N-(3-methylbenzyl)-2-(2-(phenylsulfonyl)ethylthio)nicotinamide
5   N-(4-methylbenzyl)-2-(2-(phenylsulfonyl)ethylthio)nicotinamide
6   2-(2-(phenylsulfonyl)ethylthio)-N-(2-(trifluoromethyl)benzyl)nicotinamide
7   2-(2-(phenylsulfonyl)ethylthio)-N-(pyridine-3-ylmethyl)nicotinamide
8   N-(3,5-difluorobenzyl)-2-(2-(phenylsulfonyl)ethylthio)nicotinamide
9   N-methyl-N-phenethyl-2-(2-(phenylsulfonyl)ethylthio)nicotinamide
10  N-(3-methoxybenzyl)-N-methyl-2-(2-(phenylsulfonyl)ethylthio)nicotinamide
11  N-(2-fluorobenzyl)-2-(2-(phenylsulfonyl)ethylthio)nicotinamide
12  N-(3,4-difluorobenzyl)-2-(2-(phenylsulfonyl)ethylthio)nicotinamide
13  N-(3-bromobenzyl)-N-methyl-2-(2-(phenylsulfonyl)ethylthio)nicotinamide
14  N-(2-methoxybenzyl)-2-(2-(phenylsulfonyl)ethylthio)nicotinamide
15  N-(3-fluorobenzyl)-2-(2-(phenylsulfonyl)ethylthio)nicotinamide
16  N-(furan-2-ylmethyl)-N-methyl-2-(2-(phenylsulfonyl)ethylthio)nicotinamide
17  N-(4-methoxybenzyl)-2-(2-(phenylsulfonyl)ethylthio)nicotinamide
18  N-(2-chlorobenzyl)-2-(2-(phenylsulfonyl)ethylthio)nicotinamide
19  N-(3,4-dichlorobenzyl)-2-(2-(phenylsulfonyl)ethylthio)nicotinamide
20  N-(4-fluorobenzyl)-2-(2-(phenylsulfonyl)ethylthio)nicotinamide
21  N-(2-methoxyphenethyl)-2-(2-(phenylsulfonyl)ethylthio)nicotinamide
22  N-(2,6-difluorobenzyl)-2-(2-(phenylsulfonyl)ethylthio)nicotinamide
23  N-(2-methylbenzyl)-2-(2-(phenylsulfonyl)ethylthio)nicotinamide
24  N-(3,5-dimethoxybenzyl)-2-(2-(phenylsulfonyl)ethylthio)nicotinamide
25  N-(3-chlorobenzyl)-2-(2-(phenylsulfonyl)ethylthio)nicotinamide
26  N-(2,4-dichlorobenzyl)-2-(2-(phenylsulfonyl)ethylthio)nicotinamide
29  N-(4-chlorobenzyl)-2-(2-(phenylsulfonyl)ethylthio)nicotinamide
30  N-(2,3-dichlorobenzyl)-2-(2-(phenylsulfonyl)ethylthio)nicotinamide
31  N-(4-bromobenzyl)-N-methyl-2-(2-(phenylsulfonyl)ethylthio)nicotinamide
32  N-((1,3-dioxolan-2-yl)methyl)-N-methyl-2-(2-(phenylsulfonyl)ethylthio)-nicotinamide
33  N-benzyl-N-methyl-2-(2-tosylethylthio)nicotinamide
34  N-(pyridin-2-ylmethyl)-2-(2-tosylethylthio)nicotinamide
35  N-(pyridin-4-ylmethyl)-2-(2-tosylethylthio)nicotinamide
36  N-(thiophen-2-ylmethyl)-2-(2-tosylethylthio)nicotinamide
37  N-(3-fluorophenethyl)-2-(2-tosylethylthio)nicotinamide
38  N-methyl-N-(3-methylbenzyl)-2-(2-tosylethylthio)nicotinamide
39  N-(furan-2-ylmethyl)-2-(2-tosylethylthio)nicotinamide
40  N-(pyridin-3-ylmethyl)-2-(2-tosylethylthio)nicotinamide
41  N-(3,5-difluorobenzyl)-2-(2-tosylethylthio)nicotinamide
42  N-(3-methoxybenzyl)-N-methyl-2-(2-tosylethylthio)nicotinamide
43  N-(2-fluorobenzyl)-2-(2-tosylethylthio)nicotinamide
44  N-(3-methylbenzyl)-2-(2-tosylethylthio)nicotinamide
45  N-(3,4-difluorobenzyl)-2-(2-tosylethylthio)nicotinamide
46  N-(3-bromobenzyl)-N-methyl-2-(2-tosylethylthio)nicotinamide
47  N-(4-methoxybenzyl)-2-(2-tosylethylthio)nicotinamide 48 N-(2-chlorobenzyl)-2-(2-tosylethylthio)nicotinamide
49 N-(4-fluorobenzyl)-2-(2-tosylethylthio)nicotinamide
50 N-(3,5-dimethoxybenzyl)-2-(2-tosylethylthio)nicotinamide
51 N-(3-chlorobenzyl)-2-(2-tosylethylthio)nicotinamide
52 2-(2-tosylethylthio)-N-(3-(trifluoromethyl)benzyl)nicotinamide
54 N-benzyl-2-(2-(phenylsulfonyl)ethylthio)nicotinamide
55 N-benzyl-N-methyl-2-(2-(phenylsulfonyl)ethylthio)nicotinamide
56 N-(cyclohexylmethyl)-2-(2-(phenylsulfonyl)ethylthio)nicotinamide
57 2-(2-(phenylsulfonyl)ethylthio)-N-(1-(3-(trifluoromethyl)phenyl)ethyl)-nicotinamide
58 N-(2-cyclohexylethyl)-2-(2-(phenylsulfonyl)ethylthio)nicotinamide
59 2-(2-(cyclohexylthio)ethylthio)-N-(thiophen-2-ylmethyl)nicotinamide
60 N-(neopentyl)-2-(2-(phenylsulfonyl)ethylthio)nicotinamide
61 N-(5-methylfuran-2-ylmethyl)-2-(2-(phenylsulfonyl)ethylthio)nicotinamide
62 N-(furan-2-ylmethyl)-2-(2-(phenylsulfonyl)ethylthio)nicotinamide
63 2-(2-(phenylsulfonyl)ethylthio)-N-(tetrahydro-2H-pyran-4-ylmethyl)-nicotinamide
64 2-(2-(phenylsulfonyl)ethylthio)-N-(4-(trifluoromethylthio)benzyl)-nicotinamide
65 2-(2-(phenylsulfonyl)ethylthio)-N-(3-tolylmethyl)nicotinamide
66 (R)—N-(1-cyclohexylethyl)-2-(2-(phenylsulfonyl)ethylthio)nicotinamide
67 N-(1-(3,4-dimethylphenyl)ethyl)-2-(2-(phenylsulfonyl)ethylthio)-nicotinamide
68 N-(1-thiophen-2-ylethyl)-2-(2-(phenylsulfonyl)ethylthio)nicotinamide
69 N-(1-(3,5-dimethylphenyl)methyl)-2-(2-(phenylsulfonyl)ethylthio)-nicotinamide
70 N-(cyclohexylmethyl)-2-(2-(3-trifluoromethylphenylsulfonyl)ethylthio)-nicotinamide
71 (S)—N-(1-cyclohexylethyl)-2-(2-(phenylsulfonyl)ethylthio)nicotinamide
72 N-(1-(3,5-dimethylphenyl)ethyl)-2-(2-(phenylsulfonyl)ethylthio)-nicotinamide
73 N-(thiophen-2-ylmethyl)-2-(2-(3-(trifluoromethyl)phenylthio)ethylthio)-nicotinamide
74 N-(cyclopentylmethyl)-2-(2-(phenylsulfonyl)ethylthio)nicotinamide
75 N-(cyclobutylmethyl)-2-(2-(phenylsulfonyl)ethylthio)nicotinamide
76 N-((1,4-dioxan-2-yl)methyl)-2-(2-(phenylsulfonyl)ethylthio)nicotinamide
77 2-(2-(phenylsulfonyl)ethylthio)-N-(4-(pyridin-2-yloxy)benzyl)nicotinamide
78 N-(2-methylbutyl)-2-(2-(phenylsulfonyl)ethylthio)nicotinamide
79 N-(2-ethylbutyl)-2-(2-(phenylsulfonyl)ethylthio)nicotinamide
80 N-(cyclopropylmethyl)-2-(2-(phenylsulfonyl)ethylthio)nicotinamide
81 N-(3-(2-methoxyethoxy)propyl)-2-(2-(phenylsulfonyl)ethylthio)nicotinamide
82 2-(2-(phenylsulfonyl)ethylthio)-N-(1-(4-(trifluoromethylthio)phenyl)ethyl)-nicotinamide
83 N-(3-(1H-pyrazol-1-yl)benzyl)-2-(2-(phenylsulfonyl)ethylthio)nicotinamide
84 N-((2,3-dihydrobenzofuran-5-yl)methyl)-2-(2-(phenylsulfonyl)ethylthio)-nicotinamide
85 N-(4-phenoxybenzyl)-2-(2-(phenylsulfonyl)ethylthio)nicotinamide
86 N-(1R,2S,5R)-6,6-dimethylbicyclo[3.1.1]heptan-2-yl)methyl)-2-(2-(phenyl-sulfonyl)ethylthio)nicotinamide
87 N-(thiophen-2-ylmethyl)-2-(2-(3-(trifluoromethyl)phenylsulfonyl)ethylthio)-nicotinamide
88 2-(2-(phenylsulfonyl)ethylthio)-N-(3-(trifluoromethyl)benzyl)nicotinamide
93 N-isobutyl-2-(2-(phenylsulfonyl)ethylthio)nicotinamide
94 2-[2-(benzenesulfonyl)ethylthio]-N-(2-tetrahydropyranylmethyl)-nicotinamide
95 2-[2-(benzenesulfonyl)ethylthio]-N-[(5-methyl-2-thienyl)methyl]-nicotinamide
96 2-[2-(benzenesulfonyl)ethylthio]-N-[(4-methyl-2-thienyl)methyl]-nicotinamide
97 N-(1-adamantylmethyl)-2-[2-(benzenesulfonyl)ethylthio]-nicotinamide
98 2-[2-(benzenesulfonyl)ethylthio]-N-[(3-morpholinophenyl)methyl]-nicotinamide
99 2-[2-(4-chlorophenyl)sulfonylethylthio]-N-(2-thienylmethyl)-nicotinamide
100 2-[2-(4-fluorophenyl)sulfonylethylthio]-N-(2-thienylmethyl)-nicotinamide
101 N-(2-thienylmethyl)-2-[2-[3-(trifluoromethoxy)phenyl]sulfonylethylthio]-nicotinamide
102 N-(2-thienylmethyl)-2-[2-[4-(trifluoromethyl)phenyl]sulfonylethylthio]-nicotinamide
103 N-(2-thienylmethyl)-2-[2-[4-(trifluoromethoxy)phenyl]sulfonylethylthio]-nicotinamide
104 2-[2-(m-tolylsulfonyl)ethylthio]-N-(2-thienylmethyl)-nicotinamide
105 2-[2-(m-tolylthio)ethylthio]-N-(2-thienylmethyl)-nicotinamide
106 2-[2-(3-fluorophenyl)sulfonylethylthio]-N-(2-thienylmethyl)-nicotinamide
107 2-[2-(benzenesulfonyl)ethylthio]-N-(3,3-dimethylbutyl)-nicotinamide
108 2-[2-(henzenesulfonyl)ethylthio]-N-(2-benzothiophenylmethyl)-nicotinamide
109 2-[2-(phenylthio)ethylthio]-N-(2-thienylmethyl)-nicotinamide
110 2-[2-(benzenesulfinyl)ethylthio]-N-(2-thienylmethyl)-nicotinamide
111 2-(2-cyclohexylsulfonylethylthio)-N-(2-thienylmethyl)-nicotinamide
112 N-(2-thienylmethyl)-2-[2-[[2-(trifluoromethyl)phenyl]thio]ethylthio]-nicotinamide
113 N-(2-thienylmethyl)-2-[2-[2-(trifluoromethyl)phenyl]sulfinylethylthio]-nicotinamide
114 N-(2-thienylmethyl)-2-[2-[2-(trifluoromethyl)phenyl]sulfonylethylthio]-nicotinamide
115 2-[2-(benzenesulfonyl)ethylthio]-N-[(5-chloro-2-thienyl)methyl]-nicotinamide
116 2-[2-(2-fluorophenyl)sulfonylethylthio]-N-(2-thienylmethyl)-nicotinamide
117 2-[2-[3,5-bis(trifluoromethyl)phenyl]sulfonylethylthio]-N-(2-thienylmethyl)-nicotinamide
118 2-[2-(3-methoxyphenyl)sulfonylethylthio]-N-(2-thienylmethyl)-nicotinamide
119 2-[2-(4-methoxyphenyl)sulfonylethylthio]-N-(2-thienylmethyl)-nicotinamide
120 2-[2-(benzenesulfonyl)ethylthio]-N-(4-tetrahydrothiopyranylmethyl)-nicotinamide 121  2-[2-(4-ethylphenyl)sulfonylethylthio]-N-(2-thienyl-methyl)-nicotinamide
122  N-(2-thienylmethyl)-2-[2-[[4-(trifluoromethyl)phenyl]thio]ethylthio]-nicotinamide
123  2-[2-(o-tolylthio)ethylthio]-N-(2-thienylmethyl)-nicotinamide
124  2-[2-[(3-fluorophenyl)thio]ethylthio]-N-(2-thienylmethyl)-nicotinamide
125  2-[2-[(3,4-difluorophenyl)thio]ethylthio]-N-(2-thienylmethyl)-nicotinamide
126  2-[2-[(2,4-difluorophenyl)thio]ethylthio]-N-(2-thienylmethyl)-nicotinamide
127  2-[2-(benzenesulfonyl)ethylthio]-N-[2-(2-thienyl)ethyl]-nicotinamide
128  2-[2-(benzenesulfonyl)ethylthio]-N-phenthyl-nicotinamide
129  2-[2-(benzenesulfonyl)ethylthio]-N-(3-phenylpropyl)-nicotinamide
130  2-[2-(3,4-difluorophenyl)sulfonylethylthio]-N-(2-thienylmethyl)-nicotinamide
131  2-[2-(2,4-difluorophenyl)sulfonylethylthio]-N-(2-thienylmethyl)-nicotinamide
132  2-[2-[(2-fluorophenyl)thio]ethylthio]-N-(2-thienylmethyl)-nicotinamide
133  2-[2-[(4-fluorophenyl)thio]ethylthio]-N-(2-thienylmethyl)-nicotinamide
134  2-[2-[(4-chlorophenyl)thio]ethylthio]-N-(2-thienylmethyl)-nicotinamide
135  2-[2-(p-tolylthio)ethylthio]-N-(2-thienylmethyl)-nicotinamide
136  2-[2-(benzenesulfonyl)ethylthio]-N-isopentyl-nicotinamide
137  2-[2-(benzenesulfonyl)ethylthio]-N-(2-cyclopropylethyl)-nicotinamide
138  2-[2-(benzenesulfonyl)ethylthio]-N-(2-cyclopentylethyl)-nicotinamide
139  N-(3,3-dimethylbutyl)-2-[2-[3-(trifluoromethyl)phenyl]sulfonylethylthio]-nicotinamide
140  N-(cyclopentylmethyl)-2-[2-[3-(trifluoromethyl)phenyl]sulfonylethylthio]-nicotinamide
141  2-[2-(benzenesulfonyl)ethylthio]-6-methyl-N-(2-thienylmethyl)-nicotinamide
142  2-[2-(benzenesulfonyl)ethylthio]-N-(2-thienylmethyl)-6-(trifluoromethyl)-nicotinamide
143  2-[2-(benzenesulfonyl)ethylthio]-6-fluoro-N-(2-thienylmethyl)-nicotinamide
144  2-[2-(benzenesulfonyl)ethylthio]-N-[(3-methylcyclohexyl)methyl]-nicotinamide
145  2-[2-(benzenesulfonyl)ethylthio]-N-(cycloheptylmethyl)-nicotinamide
146  2-[2-(benzenesulfonyl)ethylthio]-N-[(2-methylcyclohexyl)methyl]-nicotinamide
147  2-[2-(benzenesulfonyl)ethylthio]-N-[(4-methylcyclohexyl)methyl]-nicotinamide
148  2-[2-(benzenesulfonyl)ethylthio]-5-fluoro-N-(2-thienylmethyl)-nicotinamide
149  2-[2-(benzenesulfonyl)ethylthio]-5-methyl-N-(2-thienylmethyl)-nicotinamide, and
150  2-[2-(benzenesulfonyl)ethylthio]-N-(2-thienylmethyl)-5-(trifluoromethyl)-nicotinamide.

14. A pharmaceutical composition comprising a substituted nicotinamide compound corresponding to formula I

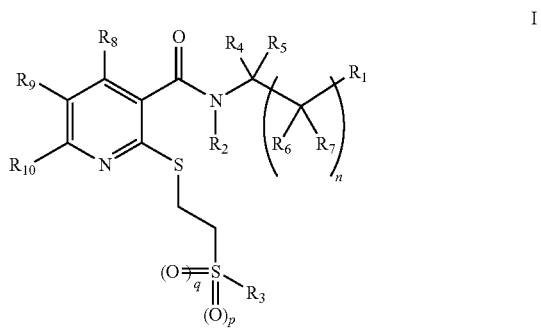

wherein
n=0, 1 or 2;
p=0 or 1;
q=0 or 1;
$R^1$ denotes aryl or heteroaryl, each unsubstituted or mono- or poly-substituted; $C_{1-6}$-alkyl, $C_{3-10}$-cycloalkyl or heterocyclyl, each unsubstituted or mono- or poly-substituted;
$R^2$ denotes H or $C_{1-6}$-alkyl, unsubstituted or mono- or poly-substituted;
$R^3$ denotes aryl or heteroaryl, unsubstituted or mono- or poly-substituted; $C_{1-6}$-alkyl or $C_{3-10}$-cycloalkyl, in each case unsubstituted or mono- or poly-substituted;
$R^4$, $R^5$, $R^6$ and $R^7$ each independently denote H or $C_{1-6}$-alkyl, unsubstituted or mono- or poly-substituted; and
$R^8$, $R^9$ and $R^{10}$ each independently denote H, F, Cl, Br, O—$C_{1-6}$-alkyl, $CF_3$, $OCF_3$, $SCF_3$, or $C_{1-6}$-alkyl;
wherein the substituents on the alkyl, heterocyclyl or cycloalkyl groups replace one or more hydrogen atoms with one or more identical or different substituents selected from the group consisting of F, Cl, Br, I, —CN, $NH_2$, NH—$C_{1-6}$-alkyl, NH—$C_{1-6}$-alkyl-OH, $C_{1-6}$-alkyl, N($C_{1-6}$-alkyl)$_2$, N($C_{1-6}$-alkyl-OH)$_2$, $NO_2$, SH, S—$C_{1-6}$-alkyl, S-benzyl, O—$C_{1-6}$-alkyl, OH, O—$C_{1-6}$-alkyl-OH, =O, O-benzyl, C(=O)$C_{1-6}$-alkyl, $CO_2H$, $CO_2$—$C_{1-6}$-alkyl, phenyl, phenoxy, morpholinyl, piperidinyl, pyrrolidinyl and benzyl; and
the substituents on the aryl or heteroaryl groups replace one or more hydrogen atoms with one or more identical or different substituents selected from the group consisting of F, Cl, Br, I, CN, $NH_2$, NH—$C_{1-6}$-alkyl, NH—$C_{1-6}$-alkyl-OH, N($C_{1-6}$-alkyl)$_2$, N($C_{1-6}$-alkyl-OH)$_2$, $NO_2$, SH, S—$C_{1-6}$-alkyl, OH, O—$C_{1-6}$-alkyl, O—$C_{1-6}$alkyl-OH, C(=O)$C_{1-6}$-alkyl, C(=O)NH$C_{1-6}$-alkyl; o-pyridyl; C(=O)-aryl; C(=O)—N-morpholine; C(=O)-piperidine; (C=O)-pyrrolidine; (C=O)-piperazine; NHSO$_2C_{1-6}$-alkyl, NHCO$C_{1-6}$-alkyl, $CO_2H$, $CH_2SO_2$-phenyl, $CO_2$—$C_{1-6}$-alkyl, $OCF_3$, $SCF_3$, $CF_3$,

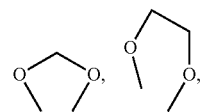

$C_{1-6}$-alkyl, pyrrolidinyl, piperidinyl, morpholinyl, benzyloxy, phenoxy, phenyl, pyridyl, alkylaryl, imidazolyl, pyrazolyl, thienyl and furyl;

or a salt thereof with a pharmacologically acceptable acid, and at least one pharmaceutically acceptable auxiliary substance.

15. A pharmaceutical composition as claimed in claim 14, wherein said substituted nicotinamide compound is selected from the group consisting of:
- 89 2-(2-(phenylsulfonyl)ethylthio)-N-(thiophen-2-ylmethyl)nicotinamide
- 90 N-(pyridin-2-ylmethyl)-2-(2-(3-(trifluoromethyl)phenylsulfonyl)ethylthio)-nicotinamide
- 91 N-(pyridin-2-ylmethyl)-2-(2-(5-(trifluoromethyl)pyridin-2-ylsulfonyl)ethyl-thio)nicotinamide, and
- 92 N-(thiophen-2-ylmethyl)-2-(2-(5-(trifluoromethyl)pyridin-2-ylsulfonyl)ethylthio)nicotinamide.

16. A method of treating or inhibiting a condition selected from the group consisting of pain, epilepsy, migraine, anxiety states, and urinary incontinence in a subject in need thereof, said method comprising administering to said subject a pharmacologically effective amount of a substituted nicotinamide compound corresponding to formula I wherein
n=0, 1 or 2;
p=0 or 1;
q=0 or 1;
$R^1$ denotes aryl or heteroaryl, each unsubstituted or mono- or poly-substituted;
$C_{1-6}$-alkyl, $C_{3-10}$-cycloalkyl or heterocyclyl, each unsubstituted or mono- or poly-substituted;
$R^2$ denotes H or $C_{1-6}$-alkyl, unsubstituted or mono- or poly-substituted;
$R^3$ denotes aryl or heteroaryl, unsubstituted or mono- or poly-substituted; $C_{1-6}$-alkyl or $C_{3-10}$-cycloalkyl, in each case unsubstituted or mono- or poly-substituted;
$R^4$, $R^5$, $R^6$ and $R^7$ each independently denote H or $C_{1-6}$-alkyl, unsubstituted or mono- or poly-substituted; and
$R^8$, $R^9$ and $R^{10}$ each independently denote H, F, Cl, Br, O—$C_{1-6}$-alkyl, $CF_3$, $OCF_3$, $SCF_3$, or $C_{1-6}$-alkyl;
wherein the substituents on the alkyl, heterocyclyl or cycloalkyl groups replace one or more hydrogen atoms with one or more identical or different substituents selected from the group consisting of F, Cl, Br, I, —CN, $NH_2$, —NH—$C_{1-6}$-alkyl, NH—$C_{1-6}$-alkyl-OH, $C_{1-6}$-alkyl, $N(C_{1-6}$-alkyl$)_2$, $N(C_{1-6}$-alkyl-OH$)_2NO_2$, SH, S—$C_{1-6}$-alkyl, S-benzyl, O—$C_{1-6}$-alkyl, OH, O—$C_{1-6}$-alkyl-OH, =O, O-benzyl, C(=O)$C_{1-6}$-alkyl, $CO_2H$, $CO_2$—$C_{1-6}$-alkyl, phenyl, phenoxy, morpholinyl, piperidinyl, pyrrolidinyl and benzyl; and
the substituents on the aryl or heteroaryl groups replace one or more hydrogen atoms with one or more identical or different substituents selected from the group consisting of F, Cl, Br, I, CN, $NH_2$, NH—$C_{1-6}$-alkyl, NH—$C_{1-6}$-alkyl-OH, $N(C_{1-6}$-alkyl$)_2$, $N(C_{1-6}$-alkyl-OH$)_2$, $NO_2$, SH, S—$C_{1-6}$-alkyl, OH, O—$C_{1-6}$-alkyl, O—$C_{1-6}$alkyl-OH, C(=O)$C_{1-6}$-alkyl, C(=O)NH$C_{1-6}$-alkyl; o-pyridyl; C(=O)-aryl; C(=O)—N-morpholine; C(=O)-piperidine; (C=O)-pyrrolidine; (C=O) piperazine; $NHSO_2C_{1-6}$-alkyl, $NHCOC_{1-6}$-alkyl, $CO_2H$, $CH_2SO_2$-phenyl, $CO_2$—$C_{1-6}$-alkyl, $OCF_3$, $SCF_3$, $CF_3$, $C_{1-6}$-alkyl, pyrrolidinyl, piperidinyl, morpholinyl, benzyloxy, phenoxy, phenyl, pyridyl, alkylaryl, imidazolyl, pyrazolyl, thienyl and furyl;
or a salt thereof with a pharmacologically acceptable acid.

17. A method as claimed in claim 16, wherein said condition is pain.

18. A method as claimed in claim 17, wherein said pain is selected from the group consisting of acute pain, chronic pain, neuropathic pain, muscular pain and inflammatory pain.

* * * * *